United States Patent
Xue et al.

(10) Patent No.: US 6,740,677 B2
(45) Date of Patent: May 25, 2004

(54) METHODS OF TREATING BENZODIAZEPINE SITE (BZD-S) ASSOCIATED SYNDROMES USING 2' HYDROXYFLAVONOIDS

(76) Inventors: Hong Xue, Flat A, 1/F, DD257, Lot No. 410-412, Tsam Chuk Wan, Sai Kung, Hong Kong (CN); Hongyan Wang, 103 Wenhua Road, Shenyang Pharmaceutical University, Shenyang, Liaoning 110015 (CN); Shing Yan Michael Huen, House 19, Seaview Villa, 18 Yin Tse Lane, Tai Po Kau, N.T., Hong Kong (CN); Kwok Min Hui, Room 2605, Hei Tsui House, Wan Tsui Estate, Chai Wan, Hong Kong (CN)

( * ) Notice: Subject to any disclaimer, the term of this patent is extended or adjusted under 35 U.S.C. 154(b) by 0 days.

(21) Appl. No.: 10/223,811

(22) Filed: Aug. 19, 2002

(65) Prior Publication Data

US 2004/0034092 A1 Feb. 19, 2004

(51) Int. Cl.[7] .............................................. A61K 31/35
(52) U.S. Cl. ..................................................... 514/456
(58) Field of Search ........................................ 514/456

(56) References Cited

U.S. PATENT DOCUMENTS

| | | | | |
|---|---|---|---|---|
| 4,065,467 A | * | 12/1977 | Doria et al. | 549/403 |
| 4,083,953 A | * | 4/1978 | Doria et al. | 424/45 |
| 4,115,567 A | * | 9/1978 | Doria et al. | 514/255.05 |
| 4,148,900 A | * | 4/1979 | Doria et al. | 514/336 |
| 4,157,334 A | * | 6/1979 | Doria et al. | 549/403 |
| 5,116,954 A | * | 5/1992 | Briet et al. | 534/551 |
| 5,399,584 A | * | 3/1995 | Ares et al. | 514/432 |
| 5,414,015 A | * | 5/1995 | Konoshima et al. | 514/456 |
| 5,707,630 A | | 1/1998 | Morrow | |
| 5,756,538 A | | 5/1998 | Cassels et al. | |
| 5,977,120 A | | 11/1999 | Giles, Jr. | |
| 6,004,998 A | | 12/1999 | Cassels et al. | |
| 6,080,410 A | | 6/2000 | Bewicke | |
| 6,080,780 A | | 6/2000 | Paladini et al. | |

OTHER PUBLICATIONS

Aqll, CA 131:240392, abstract, 1999.*
He, CA 135:55653, abstract, 2000.*
You, CA 131:29207, abstract, 1999.*
Nishikawa, A 132:149028, 1999.*
Fukai, CA 134:65794, abstract, 2000.*
Liao, Jyh–Fei, abstract of CA 129:140527, Planta Medica, 64(6), 571–572, 1998.*
Marder, M., CA 134:360986, abstract of Bioorg & Med Chem, 9(2), 323–335, Feb. 2001.*
Woods, J.H., et al., "Benzodiazepines: Use, Abuse, and Consequences", *Pharmacological Reviews*, 44(2):151–347 (1992).

Barnard, D. L. et al., "Antiherpesvirus Activity and Mode of Action of SP–303, a Novel Plant Flavonoid," *Chemotherapy* 39:203–211 (1993).
Bonetti, E.P., et al., "Benzodiazepine Antagonist Ro 15–1788: Neurological and Behavioral Effects," *Psychopharmacology* 78:8–18 (1982).
Cushman, Mark et al., "Synthesis and Protein–Tyrosine Kinase Inhibitory Activities of Flavonoid Analogues," *J. Med. Chem.* 34:798–806 (1991).
Federici, Elena et al., "Antiplasmodial Activity of the Alkaloids of *Peschiera fuchsiaefolia*," *Planta Medica* 66:93–95 (2000).
Ferriola, Patrice C. et al., "Protein Kinase C Inhibition by Plant Flavonoids," *Biochem. Pharmacol.* 38(10):1617–1624 (1989).
File, Sandra E. and Pellow, Sharon, "The effects of triazolobenzodiazepines in two animal tests of anxiety and in the holeboard," *Br. J. Pharmac.* 86:729–735 (1985).
File, Sandra E. and Pellow, Sharon, "Intrinsic actions of the benzodiazepine receptor antagonist Ro 15–1788," *Psychopharmacology* 88:1–11 (1986).
File, Sandra E. and Wardill, Ann G., "Validity of Head–Dipping as a Measure of Exploration in a Modified HoleBoard," *Psychopharmacologia (Berl.)* 44:53–59 (1975).
Hu, Hong–Zhen and Li, Zhi–Wang, "Modulation by adenosine of GABA–activated current in rat dorsal root ganglion neurons," *J. Physiology* 501.1:67–75 (1997).
Hu, H.–Z et al., "Evidence for the Existence of Substance P Autoreceptor in the Membrane of Rat Dorsal Root Ganglion Neurons," *Neuroscience* 77(2):535–541 (1997).
Hui, Kwok Min et al., "Interaction of Flavones from the Roots of *Scutellaria baicalensis* with the Benzodiazepine Site," *Planta Medica* 66:91–93 (2000).
Kimuya, Yoshiyuki et al., "Studies on Scutellariae Radix. IV. Effects on Lipid Peroxidation in Rat Liver," *Chem. Pharm. Bull.* 29(9):2610–2617 (1981).
Kubo, Michinori et al., "Studies on Scutellariae Radix," *Planta medica* 43:194–201 (1981).
Lin, Chun–Ching and Shieh, Den–En, "The Anti–inflammatory Activity of *Scutellaria rivularis* Extracts and Its Active Components, Baicalin, Baicalein and Wogonin," *American J. Chinese Med.* 24(1):31–36 (1996).
Lister, Richard G., "The use of a plus–maze to measure anxiety in the mouse," *Psychopharmacology* 92(2):180–185 (1987).

(List continued on next page.)

Primary Examiner—D. Margaret Seaman
(74) *Attorney, Agent, or Firm*—Hamilton, Brook, Smith & Reynolds, P.C.

(57) ABSTRACT

Methods for preventing or for treating benzodiazepine site (BZD-S) associated syndromes comprising administering 2' hydroxyflavone and flavone derivatives thereof which contain a hydroxyl group at the 2' position to a patient in need thereof in an effective dose. Methods for extracting certain of the compounds from plant material are also described.

18 Claims, 24 Drawing Sheets

OTHER PUBLICATIONS

Medina, Jorge H. et al., "Chrysin (5,7–DI–OH–Flavone), A Naturally–Occurring Ligand for Benzodiazepine Receptors, with Anticonvulsant Properties," *Biochem. Pharmacol.* 40(10):2227–2231 (1990).

Miksicek, Richard J., "Commonly Occurring Plant Flavonoids Have Estrogenic Activity," *Molecular Pharmacology* 44:37–43 (1993).

Nolan, Norma A. and Parkes, M.W., "The Effects of Benzodiazepines on the Behaviour of Mice on a Hole–Board," *Psychopharmacol.* 29:277–288 (1973).

Oyama, Yasuo et al., "Myricetin and quercetin, the flavonoid constituents of *Ginkgo biloba* extract, greatly reduce oxidative metabolism in both resting and $Ca^{2+}$ –loaded brain neurons," *Brain Research* 635:125–129 (1994).

Paladini, A.C. et al., "Flavonoids and the Central Nervous System: from Forgotten Factors to Potent Anxiolytic Compounds," *J. Pharm. Pharmacol.* 51(5):519–526 (1998).

Pellow, Sharon et al., "Validation of open:closed arm entries in an elevated plus–maze as a measure of anxiety in the rat," *J. Neuroscience Methods* 14:149–167 (1985).

Salgueiro, J.B., et al., "Anxiolytic Natural and Synthetic Flavonoid Ligands of the Central Benzodiazepine Receptor Have No Effect on Memory Tasks in Rats," *Pharmacol. Biochem. & Behavior* 58(4):887–891 (1997).

Sigel, Erwin et al., "The Effect of Subunit Composition of rat Brain $GABA_A$ Receptors on Channel Function," *Neuron* 5:703–711 (1990).

Sigel, E., "Effects of veratridine on single neuronal sodium channels expressed in *Xenopus oocytes*," *Pflugers Archiv— European J. Physiology* 410:112–120 (1987).

Wolfman, Claudia et al., "Possible Anxiolytic Effects of Chrysin, a Central Benzodiazepine Receptor Ligand Isolated from *Passiflora coerulea*," *Pharmacology Biochem & Behavior* 47:1–4 (1994).

Harborne, J.B. Editor, "The Flavonoids" London, Chapman & Hall, publisher:406–463 (1994).

Lim, S. S. et al., "Synthesis of Flavonoids and Their Effects on Aldose Reductase and Sorbitol Accumulation in Streptozotocin–induced Diabetic Rat Tissues," *J. Pharmacy & Pharmacology* 53 (5):653–668 (2001).

Karton, Yishai et al., "Synthesis and Biological Activities of Flavonoid Derivatives as $A_3$ Adenosine Receptor Antagonists," *J. Med. Chem.* 39:2293–2301 (1996).

Brzozowski T., et al., "Su–840, a Novel Synthetic Flavonoid Derivative of Sophoradin, with Potent Gastroprotective and Ulcer Healing Activity," *J. Physiology & Pharm.* 49(1):83–98 (1998).

Viola, H. et al., "6,3'–Dibromoflavone and 6–nitro–3'–bromoflavone; New Additions to the 6,3'–disubstituted Flavone Family of High–affinity Ligands of the Brain Benzo–diazepine Binding Site With Agonistic Properties," *Biochem. & Biophysical Res. Comm.* 273(2):694–698 (2000).

Dekermendjian, Kim et al., "Structure–Activity Relationships and Molecular Analysis of flavonoids Binding to the Benzodiazepine Site of the Rat Brain GABAA Receptor Complex," *J. Medicinal Chem.* 42(21):4343–4350 (1999).

Wolfman, Claudia et al., "Pharmacological Characterization of 6–bromo–3'–nitroflavone, a Synthetic Flavonoid With High Affinity for the Benzodiazepine Receptors," *Pharm., Biochem. & Behavior* 61(3):239–246 (1998).

Matsuura, et al., "Studies on the Nepalese Crude Drugs. On the Flavonoid and Phenylethanoid Constituents of the Root of *Scutellaria repens*", *Yakugaku Zasshi, 334(10)*:775–788 (1994) Abstract.

* cited by examiner

Compound 1

Compound 2

Compound 3

Compound 4

Compound 5

Compound 6

Compound 7

Compound 8

Compound 9

Compound 10

Compound 11

METHODS OF TREATING BENZODIAZEPINE SITE (BZD-S) ASSOCIATED SYNDROMES USING 2' HYDROXYFLAVONOIDS

BACKGROUND OF THE INVENTION

Benzodiazepines (BZDS) which bind to the benzodiazepine site (BZD-S) of the $GABA_A$ receptor are extremely effective anxiolytics, and are among the most widely prescribed psychoactive drugs in current therapeutic use. BZDs, however, also exhibit undesirable side effects including sedative and myorelaxant activity. Treatment with BZDs can also become considerably less effective over time (Woods et al., 1992, *Pharmacol. Rev.*, 44:151–347).

Certain flavonoid compounds, for example, 5,7-dihydroxyflavone (also known as chrysin) and some chrysin derivatives, also bind to the BZD-S and are known to exhibit central nervous system effects including anticonvulsant effects and anxiolytic effects without also inducing either sedative or myorelaxant effects (U.S. Pat. No. 5,756,538 to Cassels et al. (1998)). Moreover, *Scutellaria baicalensis* Georgi (commonly known as Huang Qin in Chinese and Ougon in Japanese), an important medicinal herb in traditional Chinese medicine used in the treatment of anxiety, is known to contain chrysin and other naturally-occurring flavonoid compounds.

However, most flavonoids do not bind to the BZD-S with an affinity comparable to that of the BZDs. For example, chrysin demonstrates much weaker binding to the BZD-S than does diazepam. In addition, the identification and testing of those flavonoids with optimal binding properties has been hampered by the difficulty of preparing some of them in sufficient quantity. Many naturally-occurring flavonoids are present in plant materials only in minimal amounts. Moreover, the synthesis of highly active flavonoid compounds, such as those with a plurality of hydroxyl groups, has been particularly difficult because such compounds tend to form as intermediates in the synthesis of less active compounds, rather than as an end product.

SUMMARY OF THE INVENTION

The present invention is based, at least in part, on the identification of a class of flavonoid compounds with a high affinity for the BZD-S receptor. 2' Hydroxyflavone and those 2' hydroxyflavone derivatives which also contain a hydroxyl group at the 2' position of the flavone general structure as shown in FIG. 1A, have demonstrated binding affinities for the BZD-S receptor far superior to the binding affinity of most flavonoid compounds. Some members of the class exhibit binding affinities comparable to those of BZDs, as much as one-hundred (100) times greater than that of a number of other flavonoid compounds. The high affinity of these compounds for the BZD-S receptor makes them useful for preventing and treating various central nervous system syndromes associated with the benzodiazepine site (BZD-S) of the $GABA_A$ receptor, such as anxiety and convulsions.

In one aspect, the present invention is directed to the use of the compounds of Formula I for preventing or treating a BZD-S associated syndrome:

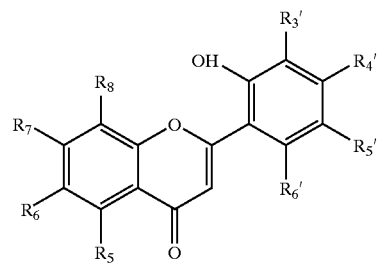

Formula I or physiologically acceptable salts thereof, wherein $R_5$, $R_6$, $R_7$, $R_8$, $R_3'$, $R_4'$, $R_5'$ and $R_6'$ are each, independently, H, OH, a $C_1$–$C_6$ alkyl, a $C_1$–$C_6$ alkenyl or a $C_1$–$C_6$ alkoxy. Alternatively, $R_5$ and $R_6$ taken together with the carbon atoms to which they are attached form a phenyl ring, which may be substituted or unsubstituted.

In particular embodiments, $R_5$ is OH, $R_6$ is OH or $R_7$ is OH. In particular embodiments $R_5$ and $R_6$ are both OH, $R_6$ and $R_7$ are both OH or $R_5$ and $R_7$ are both OH. In a particular embodiment, $R_5$, $R_6$ and $R_7$ are all OH.

In a particular embodiment, $R_8$ is a $C_1$–$C_6$ alkoxy. In a particular embodiment, $R_6$ and $R_8$ are both a $C_1$–$C_6$ alkoxy. In a particular embodiment, $R_6$ and $R_8$ are methoxy.

In one particular embodiment, the invention is directed to a method of preventing or treating a BZD-S associated syndrome in a patient in need thereof including administering to the patient an effective non-toxic dose of a compound comprising 5,7,2'-trihydroxy-6,8-dimethoxyflavone (K36) or a physiologically acceptable salt thereof.

In a particular embodiment, the BZD-S associated syndrome is anxiety. In another particular embodiment, the BZD-S associated syndrome is convulsions.

In embodiments, the compounds utilized in the methods of the invention can be administered in a dose of a single aliquot. In alternative embodiments, the compounds utilized in the methods of the invention can be administered in a dose of two or more aliquots.

In another aspect, the compounds utilized in the methods of the invention can be used in the manufacture of a medicament for preventing or treating anxiety. In particular embodiments, the compounds utilized in the methods of the invention can be used in the manufacture of a medicament for preventing or treating anxiety without producing sedative and/or myorelaxant effects. In another embodiment, the compounds utilized in the methods of the invention can be used in the manufacture of a medicament for preventing or treating convulsions. A pharmaceutical package comprising one or more containers can be filled with the compound utilized in the methods of the invention. The package can further include instructions for using the compound in the prevention or treatment of anxiety. The package can further include instructions for using the compound in the prevention or treatment of convulsions.

In another aspect, the invention is directed to a method of preparing a compound of Formula I including extracting the compound from plant material known to contain the compound using a solvent; filtering the extract, concentrating the extract, successively purifying the extract, identifying and collecting the fraction containing the compound, and forming crystals of the compound from the concentrated extract. The crystals formed from the concentrated extract can have a purity of from about 90–99%. The product yield can be from about 5 mg to 10 mg per kg of plant material.

In another aspect, the invention is directed to the product obtainable by the methods of the invention. The product can be contained in a pharmaceutically acceptable formulation. A pharmaceutical package comprising one or more containers can be filled with the product obtainable by the methods of the invention. The package can further include instructions for using the product in the prevention or treatment of anxiety. The package can further include instructions for using the product in the prevention or treatment of convulsions.

In yet another aspect, the invention is directed to a method of identifying one or more compounds useful for preventing or treating a BZD-S associated syndrome, comprising assaying a population of compounds of varied chemical structure to determine the binding affinity exhibited by each compound for BZD-S; comparing the binding affinity exhibited by each member of the population of compounds for BZD-S binding affinity; and selecting at least one compound which contains the chemical structure that provides the strongest BZD-S binding affinity, wherein a compound that exhibits strong BZD-S binding affinity is useful for preventing or treating a BZD-S associated syndrome. The method of assaying the population of compounds can comprise determining the $IC_{50}$ and $K_1$ values of the members of the population of compounds. The method of assaying the population of compounds can further comprise determining the GABA ratios of the members of the population of compounds.

BRIEF DESCRIPTION OF THE DRAWINGS

The foregoing and other objects, features and advantages of the invention will be apparent from the following more particular description of preferred embodiments of the invention.

FIG. 2A is representative of a dose response curve of diazepam (DZ) in the presence/absence of 10 M GABA.

FIG. 2O is representative of a dose response curve of 2'-hydroxy-p-naphthoflavone in the presence/absence of 10 $\mu$M GABA.

DETAILED DESCRIPTION OF THE INVENTION

A description of preferred embodiments of the invention follows.

Figure 1A:
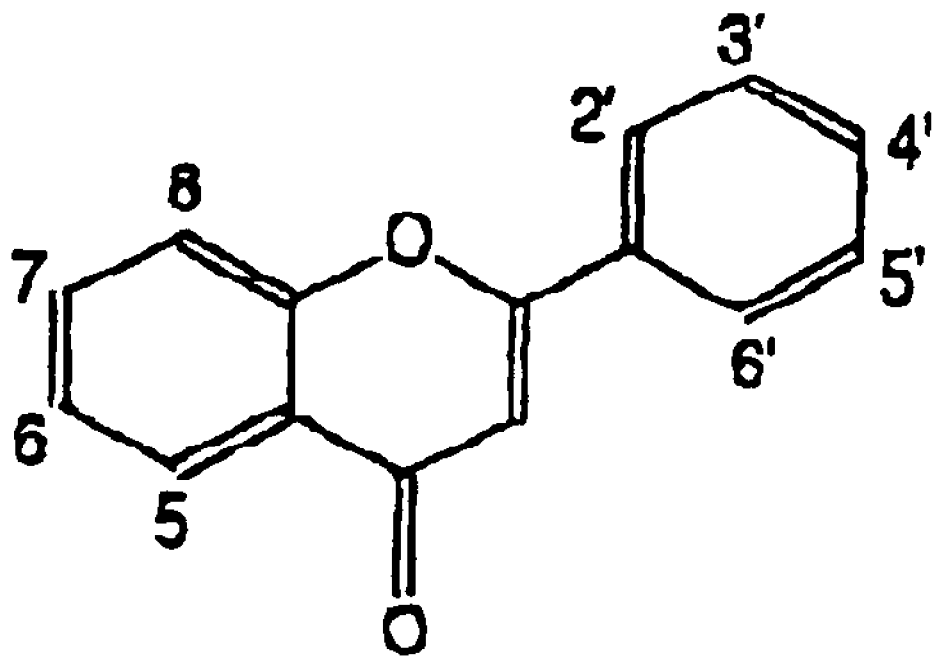
FIG. 1A is a representation of the general structure of flavone and flavone derivatives.

The present invention is based, at least in part, on the identification of a class of flavonoid compounds with a high affinity for the BZD-S receptor. 2' Hydroxyflavone and those 2' hydroxyflavone derivatives which also contain a hydroxyl group at the 2' position of the flavone general structure as shown in FIG. 1A, have demonstrated binding affinities for the BZD-S receptor far superior to the binding affinity of most flavonoid compounds. Some members of the class exhibit binding affinities comparable to those of BZDs, as much as one-hundred (100) times greater than that of a number of other flavonoid compounds. The high affinity of these compounds for the BZD-S receptor makes them useful for preventing and treating various central nervous system syndromes associated with the benzodiazepine site (BZD-S) of the $GABA_A$ receptor, such as anxiety and convulsions.

As demonstrated by the results obtained in Example 1, placement of a hydroxyl (OH) group at the 2' position of a flavone compound of Formula I dramatically increases the binding affinity of the flavone compound for the BZD-S receptor. The increased binding affinity was demonstrated both when a hydroxyl group replaced a hydrogen and when it replaced a methoxy group. An increase in binding affinity for the 2' OH substituent flavone derivatives of as much as 260 times greater than the flavone derivatives containing other substituents at the 2' position was noted. Example 7 describes a study comparing the effect of different substituents at the 2' carbon on BZD-S binding affinity. Of the substituents studied only compounds with an —$NH_2$ substitution at the 2' position demonstrated significant affinity for the BZD-S receptor.

In embodiments, the 2' hydroxyflavone compounds, as described in Formula I, can also contain hydroxyl groups at additional positions. In particular embodiments, an additional hydroxyl group can be contained at $R_5$, $R_6$ or $R_7$ In embodiments, more than one position can contain additional hydroxyl groups. In particular embodiments, $R_5$ and $R_6$, $R_6$ and $R_7$ or $R_5$ and $R_7$ can both contain additional hydroxyl groups. In embodiments, the 2' hydroxyflavone compounds, as described in Formula I, can also contain alkoxy groups. In particular embodiments, $R_6$ or $R_8$ can contain a $C_1$–$C_6$ alkoxy group. In particular embodiments, $R_6$ or $R_8$ can contain a methoxy group. In particular embodiments, $R_6$ and $R_8$ can both contain a $C_1$–$C_6$ alkoxy group. In particular embodiments, $R_6$ and $R_8$ can contain a methoxy group.

The flavenoid compounds of Formula I can be used in the prevention and treatment of various central nervous system effects associated with the BZD-S receptor. The phrase "BZD-S associated syndrome" as used herein means an effect on the central nervous system of a mammal which is affected by modulating the binding state of the benzodiazepine site (BZD-S) of the $GABA_A$ receptor. Such syndromes include anxiety and convulsions. The flavonoid compounds of Formula I can be used in the prevention and treatment of anxiety. Not only can they diminish the symptoms associated with anxiety, but many can do so without producing undesirable sedative or myorelaxant effects. The flavonoid compounds of Formula I can be used in the prevention and treatment of convulsions. In general, the compounds can be administered to a patient suffering from anxiety or convulsions in an effective non-toxic dose. Although the compounds can be administered by a variety of methods, including oral, rectal, nasal, vaginal and parenteral, oral delivery is generally preferred.

The phrase "an effective non-toxic dose" as used herein means that amount of the compound, or the physiological or pharmaceutical composition comprising the compound which is effective for the compound to provide its intended function, e.g., to provide anxiolytic treatment or anticonvulsant treatment, while not causing toxic side effects. The effective non-toxic dose can vary depending on such factors as the size and age of the patient and the severity of the state. One of ordinary skill in the art can study the aforementioned factors and make a determination regarding an effective non-toxic dose without undue experimentation.

Based on the results of the studies contained herein, it is demonstrated that the compounds can be useful in treating both acute episodes of anxiety and chronic anxiety states. Such compounds can be suitable for administration both when large doses are required, and when smaller doses extend over long periods of time. For example, the compounds can be administered in a single large dose to treat a patient experiencing a "panic attack", a type of crisis state associated with some types of anxiety. The compounds can also be administered in smaller doses provided over a period of time to control anxiety. In a particular embodiment, the compounds can be administered prior to surgery to alleviate anxiety and to induce a state of relaxation in the patient. Such treatment not only diminishes the pre-surgical stress experienced by the patient, but can minimize the amount of general anesthesia which must be administered during the surgical procedure.

Based on the results from the in vivo studies described in Example 4, the ability of K36 or its bioactive metabolites to penetrate the blood brain barrier after absorption has been demonstrated. In addition, anxiolysis of K36 was shown to be more marked than that of the common benzodiazepine anxiolytic agent diazepam at the tested dosage.

In tests where cognitive/sedative effects were assayed, diazepam and the higher doses of K36 caused significant increase in the number of head-dips, time spent headdipping and the number of rearings. Accordingly, neither diazepam nor K36 caused significant decrease in these parameters, suggesting the lack of sedative effects at the dosage regimen. In the horizontal wire test, only mice treated with the higher dose of diazepam exhibited a reduced ability to grasp the wire, while the ability of the other mice including those treated with K36 remained unchanged.

Therefore, K36, one of the compounds of the invention, has been shown to possess anxiolytic effects without the sedative and myorelaxation effects often seen in classical benzodiazepines and other non-benzodiazepine anxiolytic agents at the dosage regimen.

The compounds can be administered without further additions, or they can be admixed with various pharmaceutically or physiologically acceptable components. The phrase "pharmaceutically or physiologically acceptable" as used herein refers to those compounds, compositions containing such compounds, and/or dosage forms which are, within the scope of sound medical judgments, suitable for use.

The compounds of the present invention can exist in free form or, where appropriate, in salt form. Certain salt forms are particularly desirable when enhanced solubility is required. Pharmaceutically or physiologically acceptable salts and their preparation are well-known to those of skill in the art. The pharmaceutically acceptable salts of such compounds include the conventional non-toxic salts formed from sodium, calcium and magnesium or the quaternary ammonium salts of such compounds which are formed, for example, from inorganic or organic acids or bases.

The invention also relates to pharmaceutical or physiological compositions comprising a therapeutically effective amount of the compounds and a pharmaceutical carrier or excipient. Carriers include, e.g., saline, buffered saline, dextrose, water, glycerol, ethanol, and combinations thereof. The composition, if desired, can also contain minor amounts of wetting or emulsifying agents, or pH buffering agents. The composition can be a liquid solution, suspension, emulsion, tablet, pill, capsule, sustained release formulation or powder. The composition can be formulated as a suppository, with conventional binders and carriers such as triglycerides. Oral formulations can include standard carriers such as pharmaceutical grades of mannitol, lactose, starch, magnesium stearate, sodium saccharine, cellulose, magnesium carbonate and others known to those of skill in the art. The pharmaceutical carrier may be either a solid or a liquid.

Illustrative solid carriers include lactose, terra alba, sucrose, talc, gelatin, agar, pectin, acacia, magnesium stearate, stearic acid, and the like. A solid carrier can include one or more substances which may also act as flavoring agents, lubricants, solubilizers, suspending agents, filler, glidants, compression aids, binders or tablet disintegrating agents; it can also be an encapsulating material. In powders, the carrier is a finely divided solid which is in admixture with the finely divided active ingredient. In tablets, the compound is mixed with a carrier having the necessary compression properties in suitable proportions, and compacted in the shape and size desired.

Illustrative liquid carriers include syrup, peanut oil, olive oil, water and the like. Liquid carriers are used in preparing solutions, suspensions, emulsions, syrups and elixirs. The composition can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators and stabilizers.

A wide variety of pharmaceutical forms can be employed. If a solid carrier is used, the preparation can be tableted, placed in a hard gelatin capsule in powder or pellet form or in the form of a troche or lozenge. If a liquid carrier is use, the preparation will be in the form of a syrup, emulsion or soft gelatin capsule.

The compounds can be conveniently supplied in standard pharmaceutical packaging. Such containers are well known in the art. Instructions for the proper use of the compounds as a medicament or for the particular use of the compounds as a medicament in the prevention or treatment of anxiety or convulsions can be supplied with the packaging.

Methods for efficiently extracting the flavonoid compounds in high purity from the vegetive portions of plant materials are provided. A particular method includes extracting the compounds from the roots of the *Scutellaria baicalensis* Georgi herb where many are contained in some quantity. Example 5 illustrates the use of this method to prepare 5,7,2'-trihydroxy-6-8-dimethoxyflavone (K36). Other portions of the *Scutellaria baicalensis* Georgi herb can also be utilized in the process, as can other herbs which contain the compounds. Table 1 provides a non-limiting list of herbs likely to contain useful flavonoids.

TABLE 1

Plants of the Genus Scutellaria

*Scutellaria baicalensis* Georgi
*S. amonea* C. H. Wright
*S. barbata* D. Don (*S. rivularis* Wall)
*S. hypericifolia* Levl.
*S. indica* L.
*S. likiangensis* Diels
*S. planipes*
*S. rehderiana* Diels
*S. strigillosa* Hemsl.

TABLE 1-continued

*S. tenax* W. W. Smith var. *patentipilosa*
*S. viscidula* Bunge
Plants of other Genera

*Sorbaria sorbifolia*
*Tetracera indica*

The herb can be formed into a fine powder by crushing, grinding or other methods prior to the extraction of the compound. The extraction process can utilize a chlorinated solvent such as dichloromethane or chloroform or an alcohol such as methanol, ethanol or n-butanol. Ethyl ether, acetone and ethyl acetate as well as other solvents known in the art are also suitable for use in the methods of the invention. Any number of extractions can be performed including 1, 2, 3, 4, 5,6 or more extractions. The extraction can be performed at standard temperature and pressure, e.g., 25° C. and 1 atmosphere. The extraction can also be performed at other temperatures and pressures. In a particular embodiment, the extraction is performed at the boiling point of the solvent used in the extraction.

The extract can be filtered by any suitable method, including filtering with standard filter paper. The extract can also be concentrated by any suitable method, including concentration achieved through the use of an evaporator.

Crystals of the compound can be formed by dissolving the extract in a solvent, such as ethanol, and allowing it to remain at room temperature for a suitable period of time. The crystals formed can be filtered and washed with a suitable solvent, such as ethanol.

Alternative methods for producing the compounds are also within the scope of the invention including extractions with supercritical fluids such as $CO_2$. An example of an alternative method of preparing 5,7,2'-trihydroxy-6,8-dimethoxyflavone is provided in Example 6.

The methods described herein produce a product with high purity. Although the total quantity of the compound produced is often small, the amount is still quite unexpected given that the compound, which has four (4) hydroxyl groups, is quite reactive. The product produced generally has a purity range of from about 90 to about 99%, with an average purity of about 95%. Estimated yield of extraction is about 5–10 mg per kg of *Scutellaria baicalensis* root.

The flavonoid compounds of the present invention can be chemically synthesized by procedures known to those of skill in the art. The following references, for example, describe methods of synthesizing flavonoid compounds: Lim, S. S et al., "Synthesis of flavonoids and their effects on aldose reductase and sorbitol accumulation in streptozotocin-induced diabetic rat tissues.", *Journal of Pharmacy & Pharmacology.* 53(5).653-68, 2001; Constituents of *Asarum europeum L.*, Communication No. 18, "Dynamics of the synthesis of flavonoids", *Acta Pharmaceutica Hungarica.* 61(2):86–90, 1991; Viola H., et al., "6,3'-Dibromoflavone and 6-nitro-3'-bromoflavone: new additions to the 6,3'-disubstituted flavone family of high-affinity ligands of the brain benzo-diazepine binding site with agonistic properties." *Biochemical & Biophysical Research Communications.* 273(2):694–8, 2000; Wolfman C., et al., "Pharmacological characterization of 6-bromo-3'-nitroflavone, a synthetic flavonoid with high affinity for the benzodiazepine receptors.", *Pharmacology, Biochemistry & Behavior.* 61(3):239–46, 1998; Brzozowski T., et al., "SU-840, a novel synthetic flavonoid derivative of sophoradin, with potent gastroprotective and ulcer healing activity.", *Journal of Physiology & Pharmacology.* 49(1):83–98, 1998; Kim Dekermendjian, et al., "Structure-Activity Relationships and Molecular Modeling Analysis of Flavonoids Binding to the Benzodiazepine Site of the Rat Brain GABAA Receptor Complex", *Journal of Medicinal Chemistry.* 42(21):4343–4350, 1999; Jacobson, Kenneth A., "Synthesis and Biological Activities of Flavonoid Derivatives as A3 Adenosine Receptor Antagonists", *Journal of Medicinal Chemistry.* 39(12): 2293–2301, 1996;

Alternatively, some flavonoid compounds useful in the methods of the invention are commercially available. For example, 6,2'-dihydroxyflavone (Compound 3), 2'-hydroxy-β-naphthoflavone (Compound 4), 2'-hydroxyflavone (Compound 6), flavone (Compound 9), 6-hydroxy-2'methoxyflavone (Compound 11) and 2'-methoxyflavone (Compound 12) were obtained commercially from Indofine Chemical Company, Inc., Somerville, N.J. The flavenoids 5,7,2'-trihydroxy-6,8-dimethoxyflavone (K36), 5,7-dihydroxy-6-methoxyflavone (K7), 5,7-dihydroxy-6,8-methoxyflavone, 5,7-dihydroxy-8-methoxyflavone (Wogonin) and 5,6,7-trihydroxyflavone (Baicalein) utilized in the examples of this application were purified in the laboratory from the herb *Scutellaria baicalensis* Georgi. These and other flavenoids of the invention can be purified from the herb *Scutellaria baicalensis* Georgi or from other sources including those listed in Table 1.

Additional compounds useful for preventing or treating a BZD-S associated syndrome can be developed using the methods taught herein. A population of compounds of varied chemical structure can be assayed to determine the binding affinity exhibited by each compound for BZD-S. The population of compounds can be highly varied in chemical structure or can be closely related in chemical structure. Typically, the compounds are members of a family of related compounds. The compounds can be obtained from any source. The compounds can be naturally-occuring compounds or can be synthesized. The binding affinity exhibited by each member of the population of compounds for BZD-S can be determined by any method known to those of skill in the art. Such methods can include determining the $IC_{50}$ and $K_1$ values and the GABA ratios of the members of the population of compounds or any combination of one or more of those assays. Additional methods of determining the binding affinity of the members of the population of compounds can also be included. The binding affinity of each member of the population of compounds can then be compared to the chemical structure of the compound. A chemical structure represented in each member of the population of compounds that exhibits the strongest BZD-S binding affinity can be determined. The common chemical structure can be any portion of the chemical structure of the compound. At least one compound which contains the chemical structure that provides the strongest BZD-S binding affinity can be selected. Often the compound will be subjected to further testing.

The invention is further illustrated by the following non-limiting examples. The contents and teachings in their entireties of all patents, patent applications and the references cited throughout this application are expressly incorporated by reference herein.

EXAMPLE 1
Evaluation of the Structure-Activity Relationship of Selected Flavonoids Twelve different flavonoids were assayed to determine their binding affinity for BZD-S. The $IC_{50}$ and $K_1$ values for each were calculated and compared with their respective chemical structures. Candidates were selected for this experiment to illustrate the effect of the 2' OH group (see FIG. 1A and Table 2 below). Many compounds differ from each other only in the substituent contained on one side branch, i.e., the presence or absence of the 2' OH group.

Radioactive [$^3$H]-flunitrazepam (N-methyl-[$^3$H], 88.0 Ci/mmol) was purchased from Amersham. [$^3$H]-Ro15-1788 (N-methyl-[$^3$H], 70.8 Ci/mmol) was purchased from Nen Life Science Products. Diazepam was purchased from Sigma Chemical. 6,2'-dihydroxyflavone, 2'-hydroxy-β-naphthoflavone, 2'-hydroxyflavone, flavone, 6-hydroxy-2'-methoxyflavone and 2'-methoxyflavone were obtained commercially from Indofine Chemical. Other flavonoids in this study were purified in our laboratories. Other materials were of the highest grades from standard commercial sources.

TABLE 2

Selected Flavonoids

| Compound | Name | Side Chain | | | | |
|---|---|---|---|---|---|---|
| | | 2' | 5 | 6 | 7 | 8 |
| 1 | 5,7,2'-trihydroxy-6,8-dimethoxyflavone (K36) | OH | OH | OCH$_3$ | OH | OCH$_3$ |
| 2 | 5,7,2'-trihydroxy-6-methoxyflavone (K38) | OH | OH | OCH$_3$ | OH | |
| 3 | 6,2'-dihydroxyflavone | OH | | OH | | |
| 4 | 2'-hydroxy-β-naphthoflavone | OH | | *C$_4$H$_4$ | | |
| 5 | 2'-hydroxyflavone | OH | | | | |
| 6 | 5,7-dihydroxy-6,8-dimethoxyflavone | | OH | OCH$_3$ | OH | OCH$_3$ |
| 7 | 5,7-dihydroxy-6-methoxyflavone (K7) | | OH | OCH$_3$ | OH | |
| 8 | 5,7-dihydroxy-8-methoxyflavone (Wogonin) | | OH | | OH | OCH$_3$ |
| 9 | flavone | | | | | |
| 10 | 5,6,7-trihydroxyflavone (Baicalein) | | OH | OH | OH | |
| 11 | 6-hydroxy-2'-methoxyflavone | OCH$_3$ | | OH | | |
| 12 | 2-methoxyflavone | OCH$_3$ | | | | |

Radioligand Receptor Binding Procedure

A radioligand receptor binding experiment was carried out as described previously (see Schacht and Baecker, 1982: Vogel, et al., 1997) for the twelve compounds. For the assay procedure, 45 μl of membrane suspension (0.8 mg/ml) was added to the incubation mixture containing 238 μl 0.05 M Tris-HCl (pH 7.4), with or without labeled test compound. Samples were incubated in duplicate for 30 minutes at 4° C. For the competition assay, a final [$^3$H]-flunitrazepine concentration of 1 nM was used.

For the saturation assay, twelve concentrations of [³H]-flunitrazepine were employed and non-specific binding was determined by the addition of 10 μM of diazepam to compete out the specific binding. After incubation, the reaction was rapidly stopped by vacuum filtration through a GF/B filter on a Millipore multi-place vacuum chamber. The filters were washed twice with 5.0 ml of 0.05 M Tris-HCl buffer and dried under vacuum. The amount of radioligand on the dried filters was determined in 5.0 ml scintillation cocktail with a Wallac 1209 Rackbeta liquid scintillation counter (with an efficiency of 48%). Specific binding was calculated by subtracting the non-specific binding from total binding.

The results were determined by non-linear regression analysis (sigmoidal curve fitting) of % control versus semi-log concentration (M). $K_1$ values were calculated using the equation $K_1 = IC_5/[1+([^3H]/K_d)]$. The data are shown in Table 3.

TABLE 3

$IC_{50}$ and $K_1$ Values Of Selected Flavonoids

| Compound | Name | Inhibition of 3H-Flunitrazepam (μM) | |
|---|---|---|---|
| | | $IC_{50}$ | $K_1$ |
| 1 | 5,7,2'-trihydroxy-6,8-dimethoxyflavone (K36) | 0.0015 | 0.0011 |
| 2 | 5,7,2'-trihydroxy-6-methoxyflavone (K38) | 0.0096 | 0.0076 |
| 3 | 6,2'-dihydroxyflavone | 0.017 | 0.013 |
| 4 | 2'-hydroxy-β-naphthoflavone | 0.055 | 0.044 |
| 5 | 2'-hydroxyflavone | 0.19 | 0.15 |
| 6 | 5,7-dihydroxy-6,8-dimethoxyflavone | 0.36 | 0.29 |
| 7 | 5,7-dihydroxy-6-methoxyflavone (K7) | 1.61 | 1.28 |
| 8 | 5,7-dihydroxy-8-methoxyflavone (Wogonin) | 2.76 | 2.19 |
| 9 | flavone | 6.86 | 5.44 |
| 10 | 5,6,7-trihydroxyflavone (Baicalein) | 10.11 | 8.03 |
| 11 | 6-hydroxy-2'-methoxyflavone | 14.51 | 11.52 |
| 12 | 2-methoxyflavone | 15.13 | 12.01 |

Dose-inhibition curves were generated with nine to twelve drug concentrations. $IC_{50}$ values for various compounds were estimated by displacement of [³H]-flunitrazepam binding to synaptosomal membrane protein extracted from whole brain of Sprague-Dawley rat (approximately 250 g). $K_1$ values were calculated according to the equation: $K_1 = IC_{50}/[1+(^3H)/K_d)]$, where [³H] is the concentration of [³H]-flunitrazepam (1 nM), and $K_d$ is the dissociation constant of [³H]-flunitrazepam from the high affinity binding site (3.86 nM).

Results

Figure 1B:
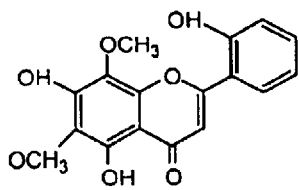
FIG. 1B is a representation of twelve (12) flavonoid compounds utilized in the examples contained in this application. The compounds are numbered according to the order of their appearance in Table 2.
Figure 1B:
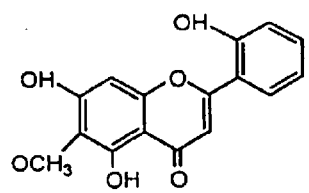
Figure 1B:
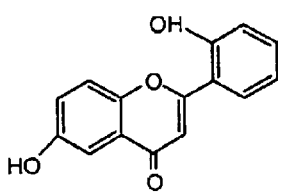
Figure 1B:
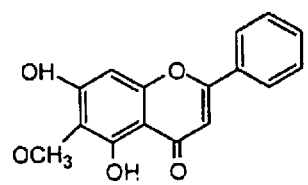
Figure 1B:
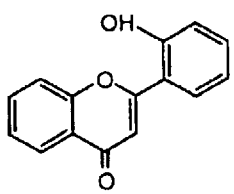
Figure 1B:
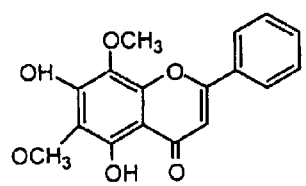
Figure 1B:
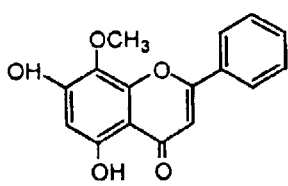
Figure 1B:
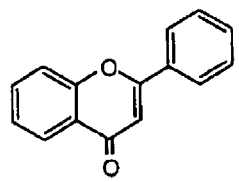
Figure 1B:
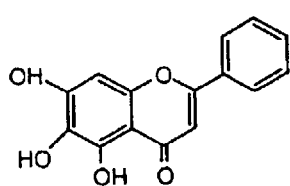
Figure 1B:
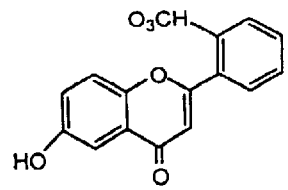
Figure 1B:
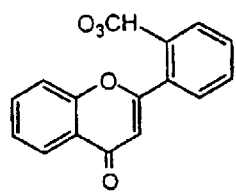
Figure 2A:
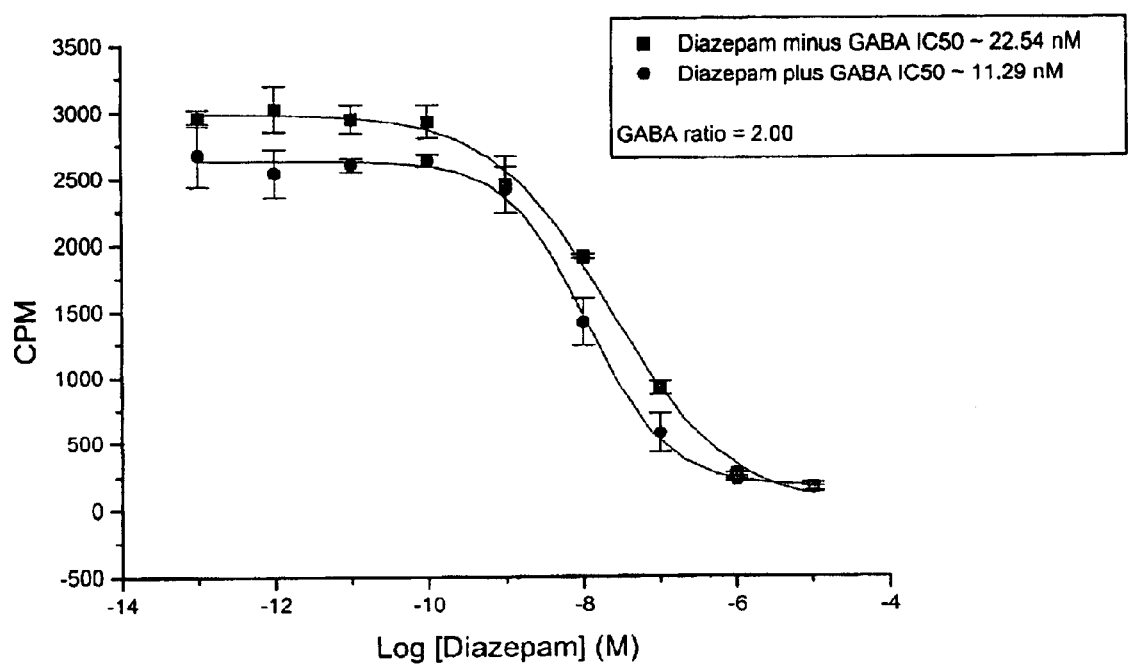
FIGS. 2A–2O are representations of the dose response curves of several flavonoid compounds in the presence or absence of GABA.
Figure 2B:
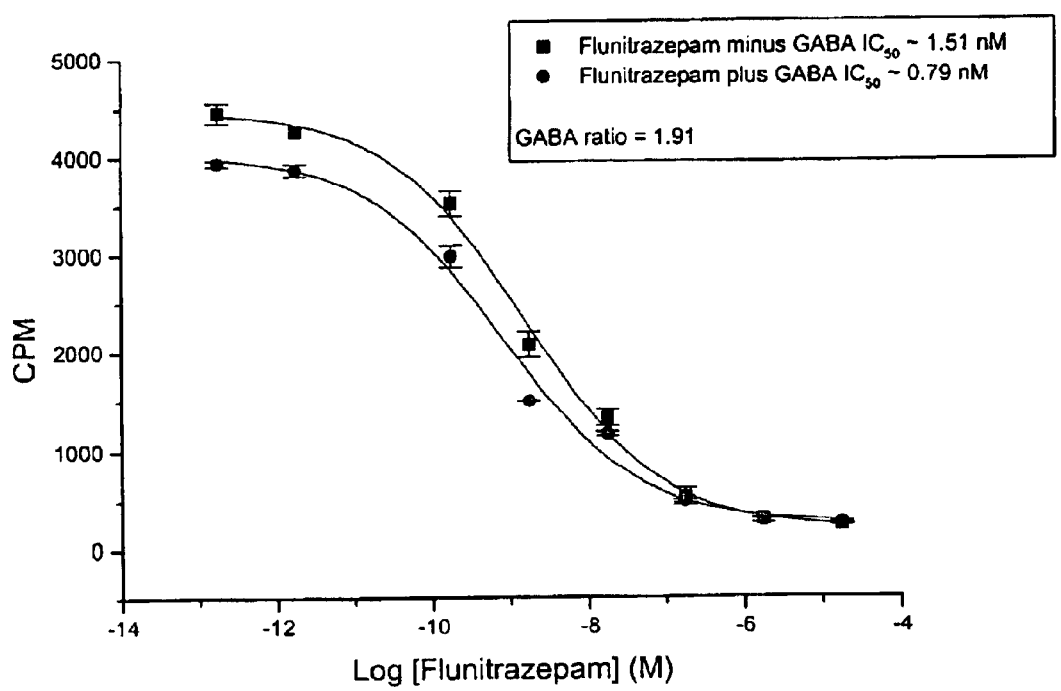
FIG. 2B is representative of a dose response curve of flunitrazepam in the presence/absence of 10 $\mu$M GABA.
Figure 2C:
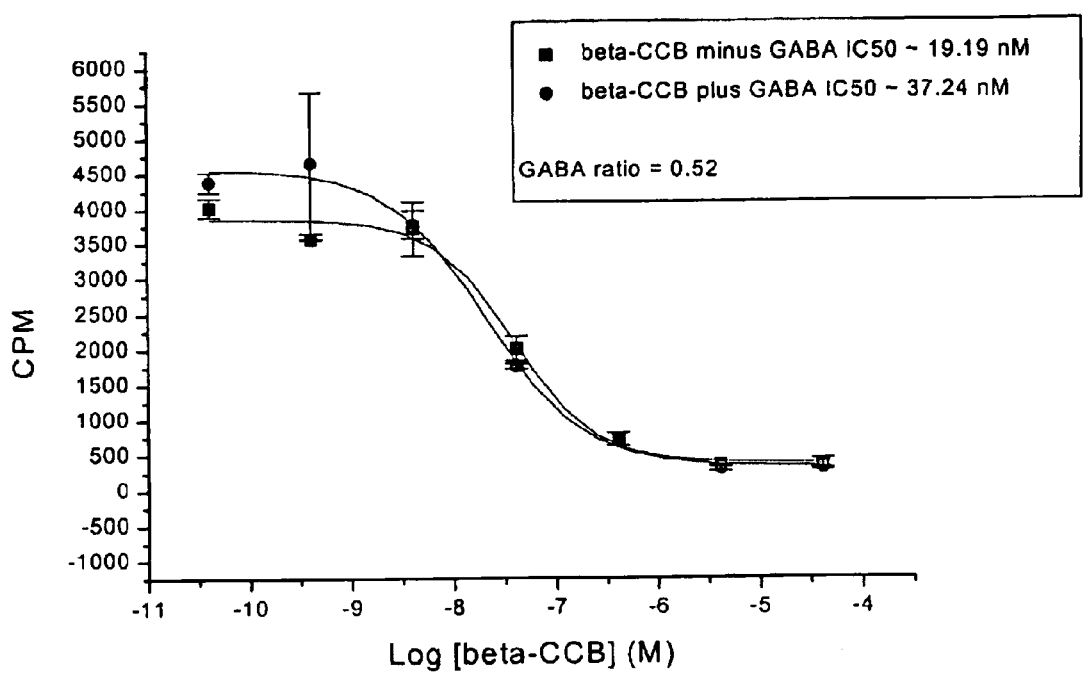
FIG. 2C is representative of a dose response curve of beta-CCB in the presence/absence of 10 $\mu$M GABA.
Figure 2D:
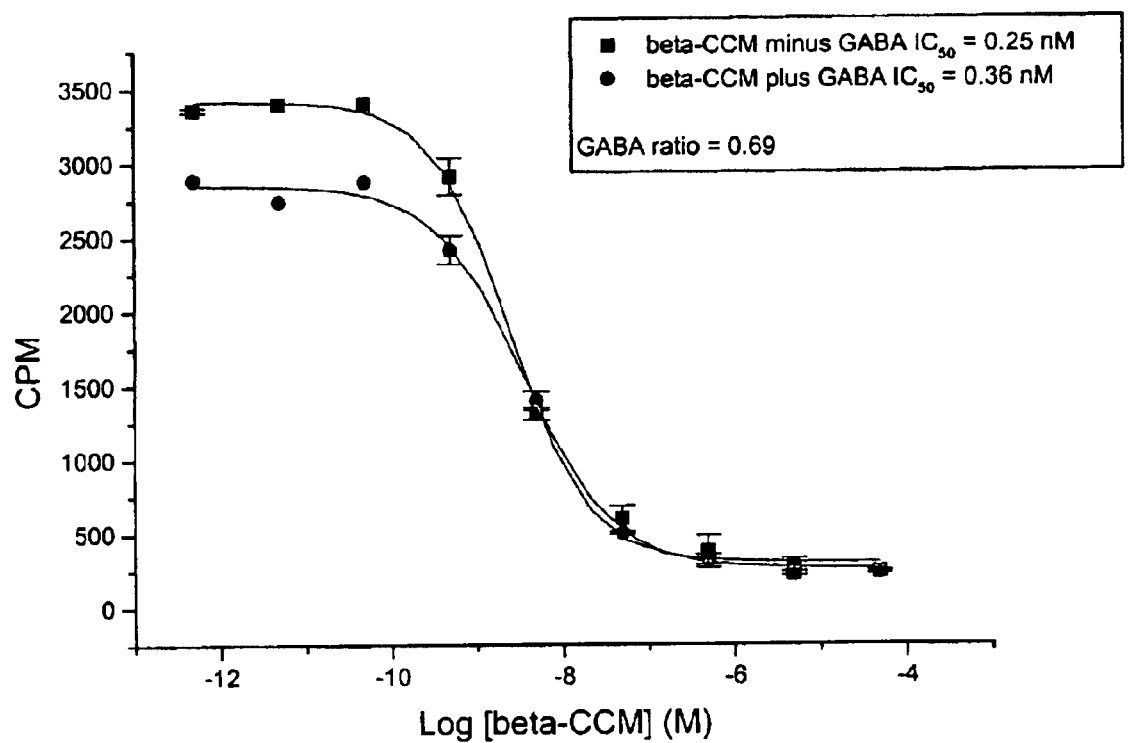
FIG. 2D is representative of a dose response curve of beta-CCM in the presence/absence of 10 $\mu$M GABA.
Figure 2E:
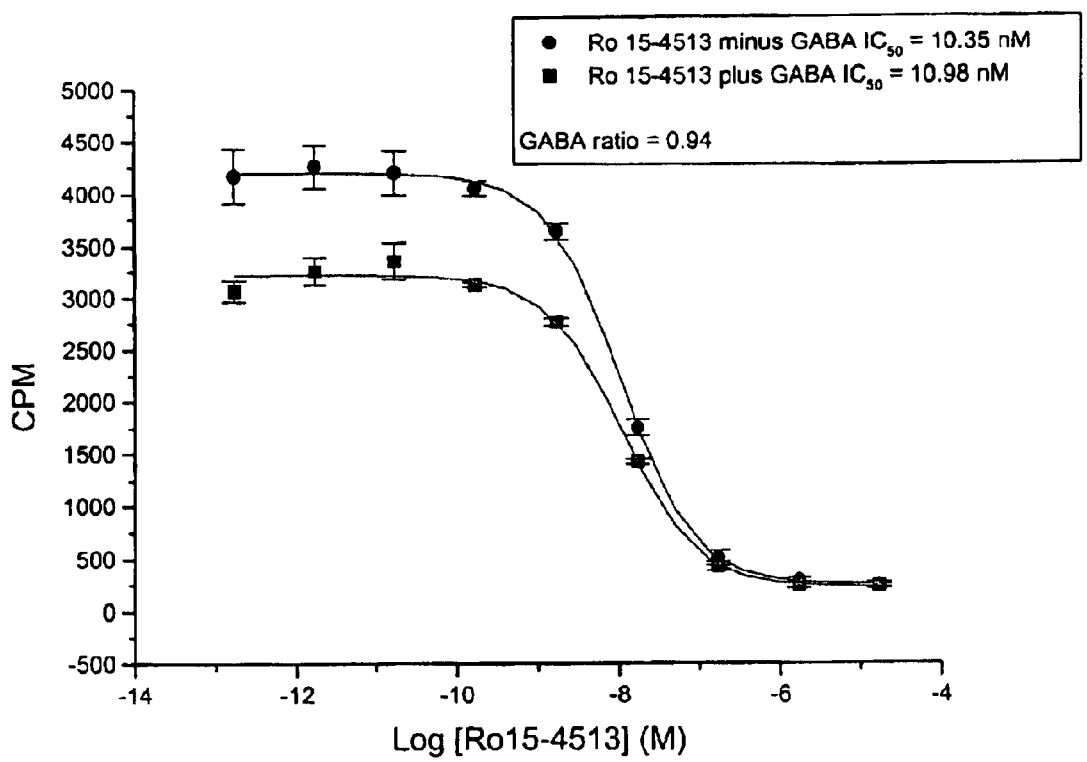
FIG. 2E is representative of a dose response curve of Ro15-4513 in the presence/absence of 10 $\mu$M GABA.
Figure 2F:
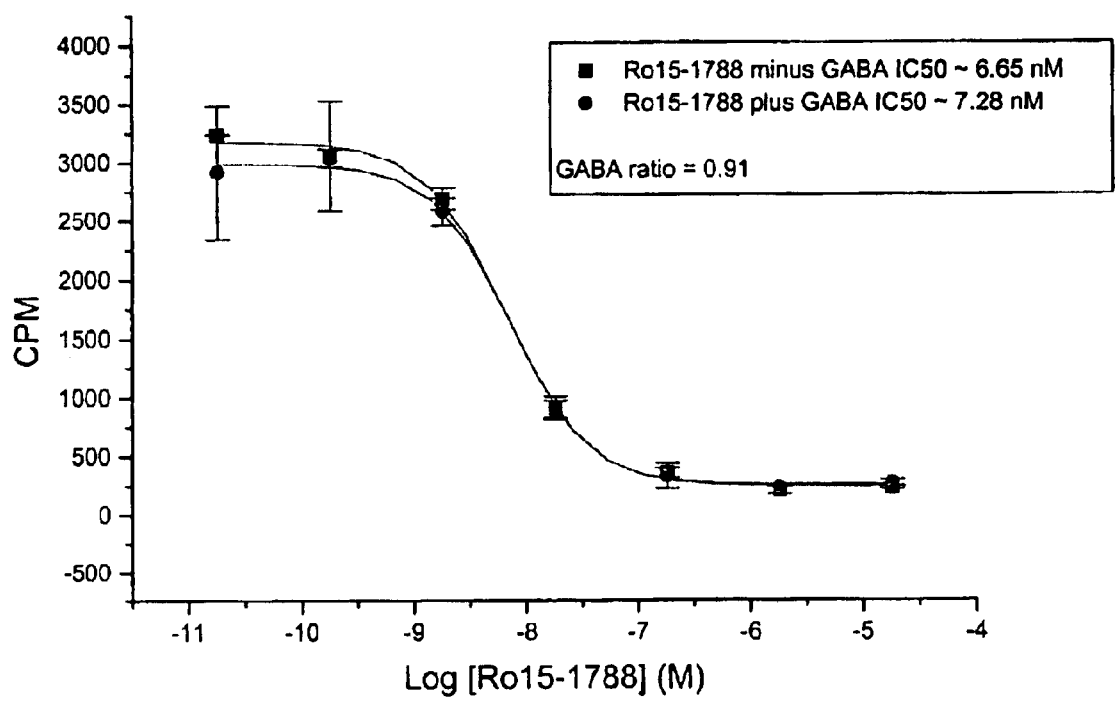
FIG. 2F is representative of a dose response curve of Ro15-1788 in the presence/absence of 10 $\mu$M GABA.
Figure 2G:
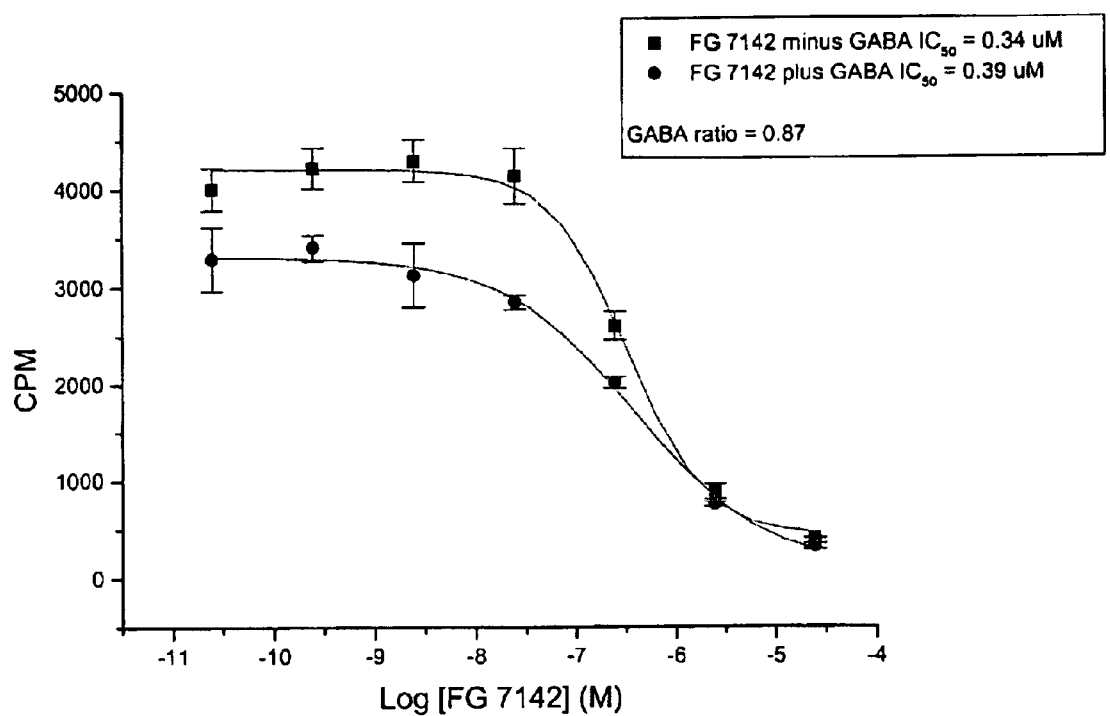
FIG. 2G is representative of a dose response curve of FG-7142 in the presence/absence of 10 $\mu$M GABA.
Figure 2H:
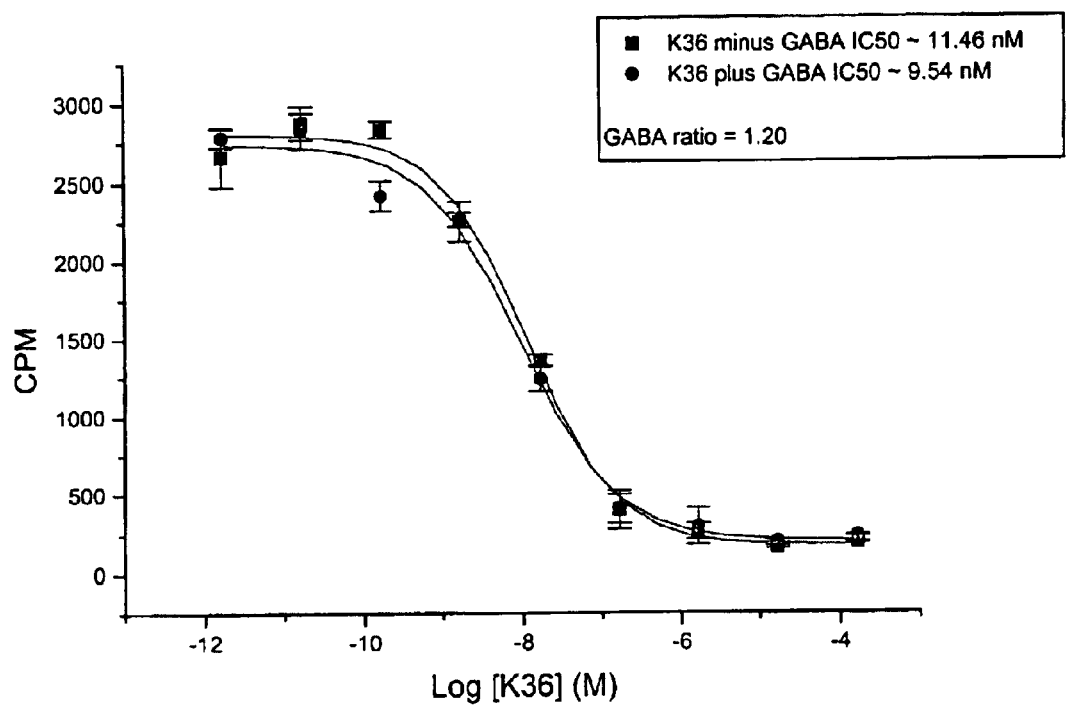
FIG. 2H is representative of a dose response curve of 5,7,2'-trihydroxy-6,8-dimethoxyflavone (K36) in the presence/absence of 10 $\mu$M GABA.
Figure 2I:
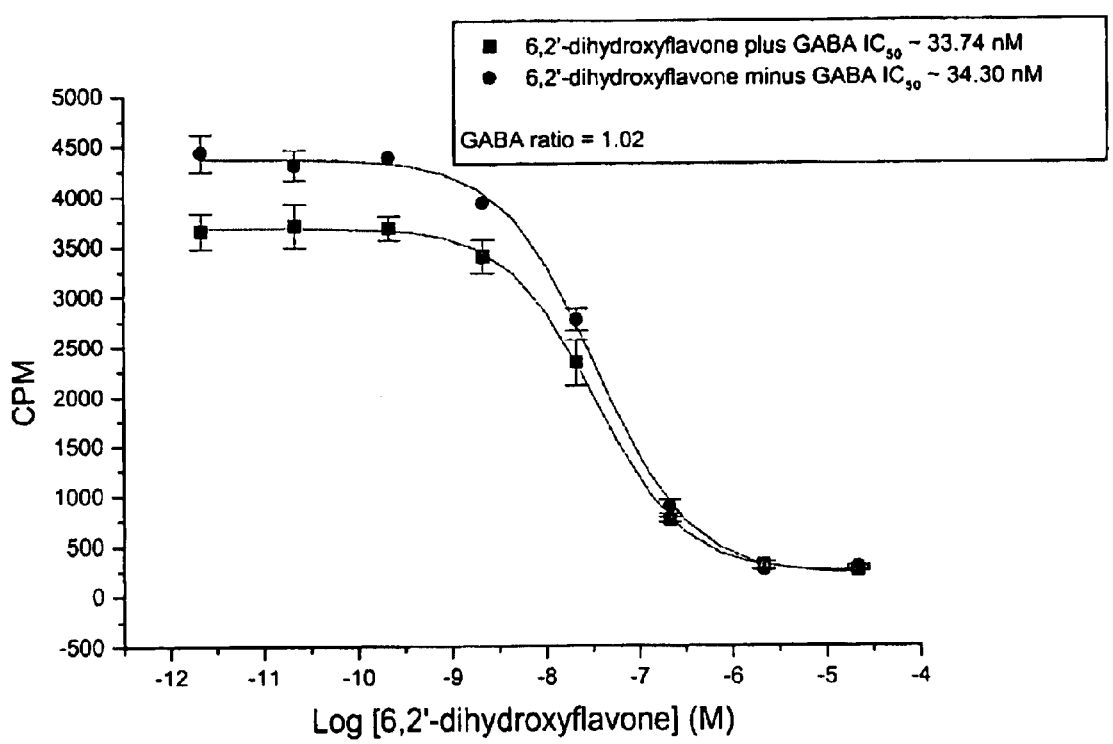
FIG. 2I is representative of a dose response curve of 6,2'-dihydroxyflavone in the presence/absence of 10 $\mu$M GABA.
Figure 2J:
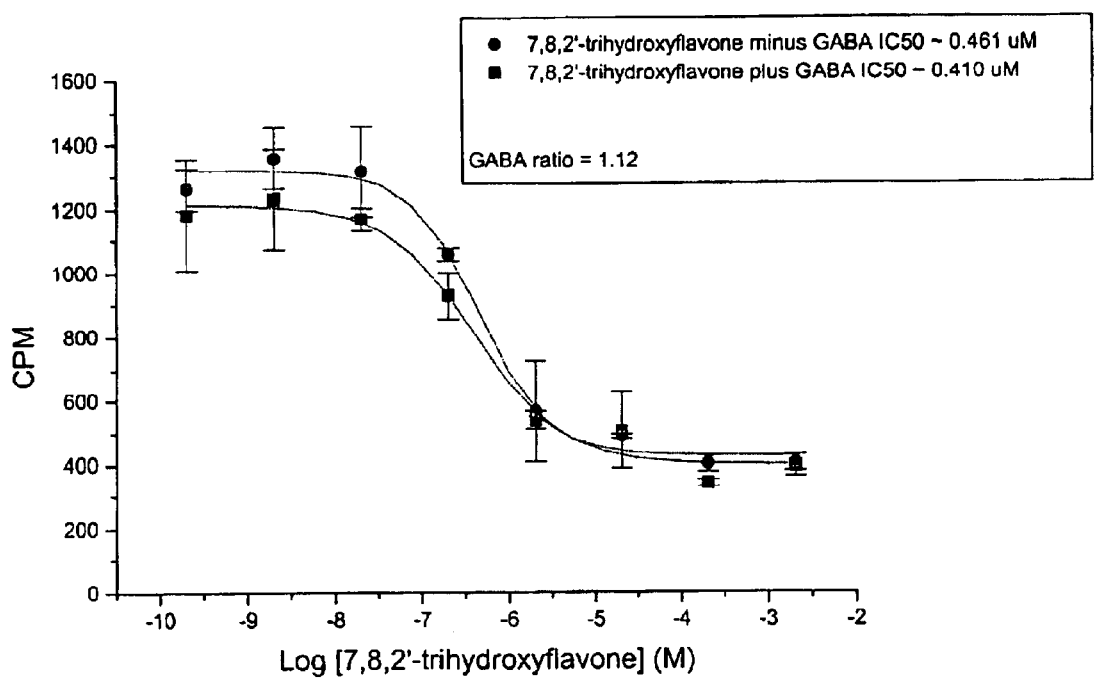
FIG. 2J is representative of a dose response curve of 7,8,2'-trihydroxyflavone in the presence/absence of 10 $\mu$M GABA.
Figure 2K:
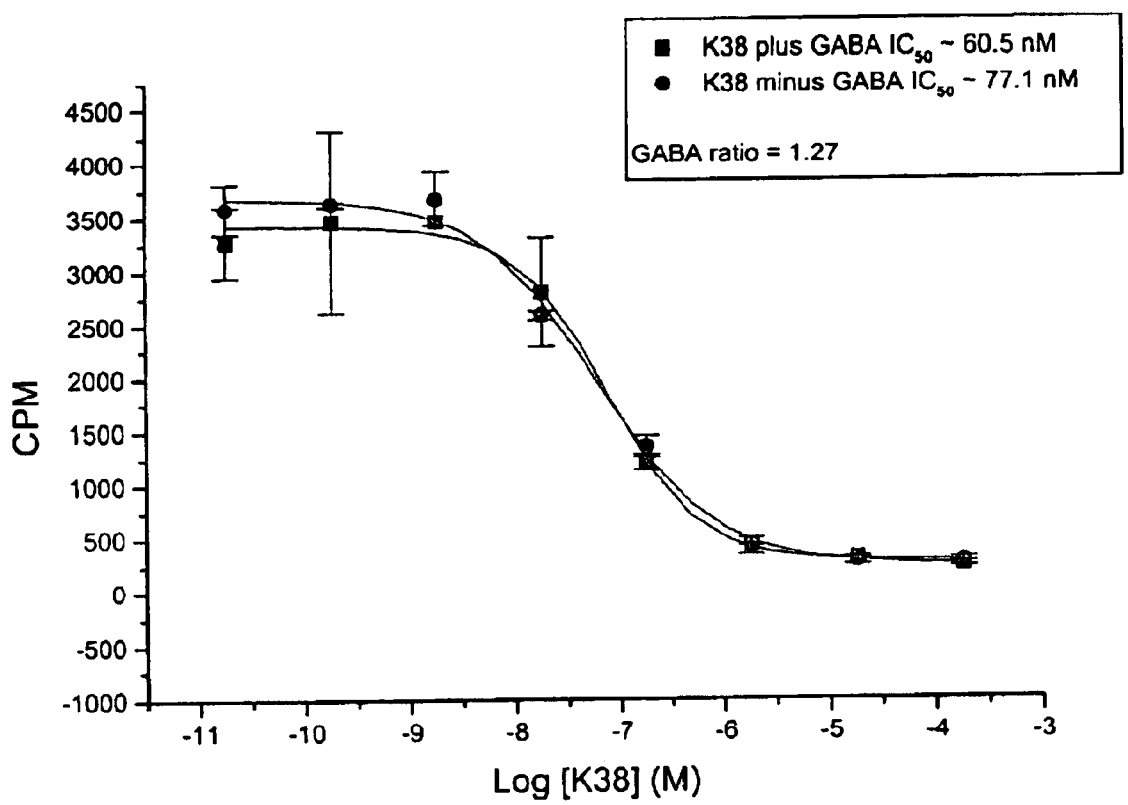
FIG. 2K is representative of a dose response curve of 5,7-dihydroxy-8-methoxyflavone (K38) in the presence/absence of 10 $\mu$M GABA.
Figure 2L:
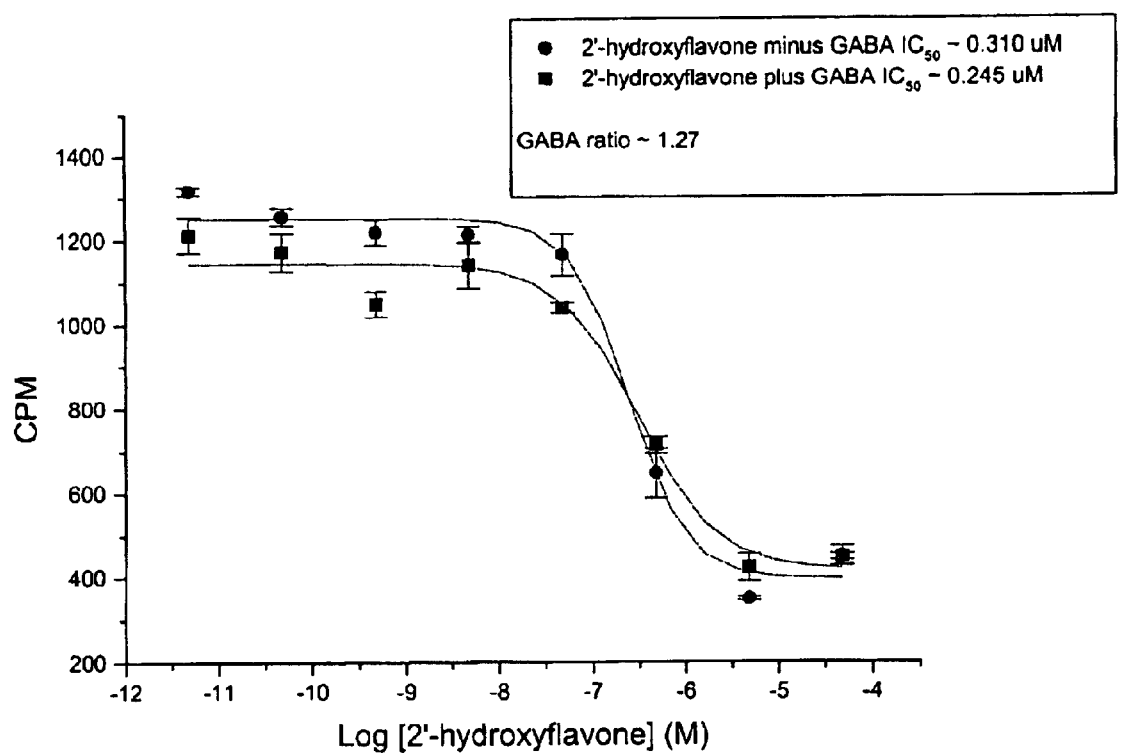
FIG. 2L is representative of a dose response curve of 2'-hydroxyflavone in the presence/absence of 10 $\mu$M GABA.
Figure 2M:
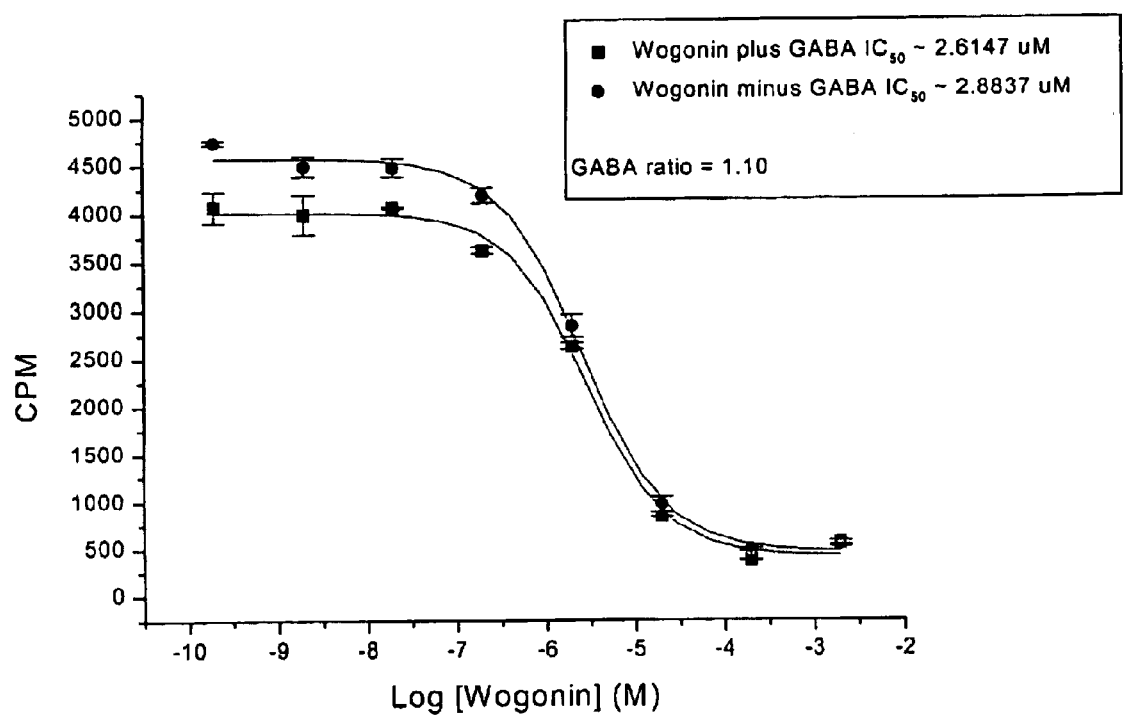
FIG. 2M is representative of a dose response curve of 5,7-dihydroxy-8-methoxyflavone (Wogonin) in the presence/absence of 10 $\mu$M GABA.
Figure 2N:
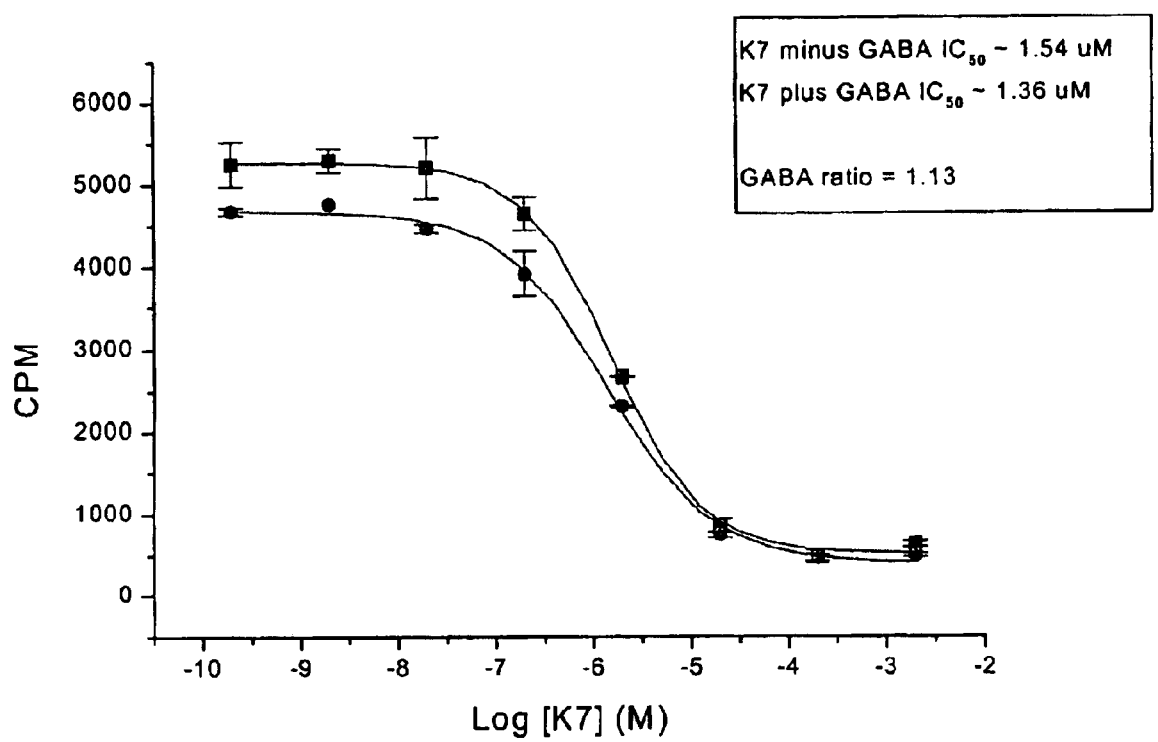
FIG. 2N is representative of a dose response curve of 5,7-dihydroxy-6-methoxyflavone (K7) in the presence/absence of 10 $\mu$M GABA.
Figure 2O:
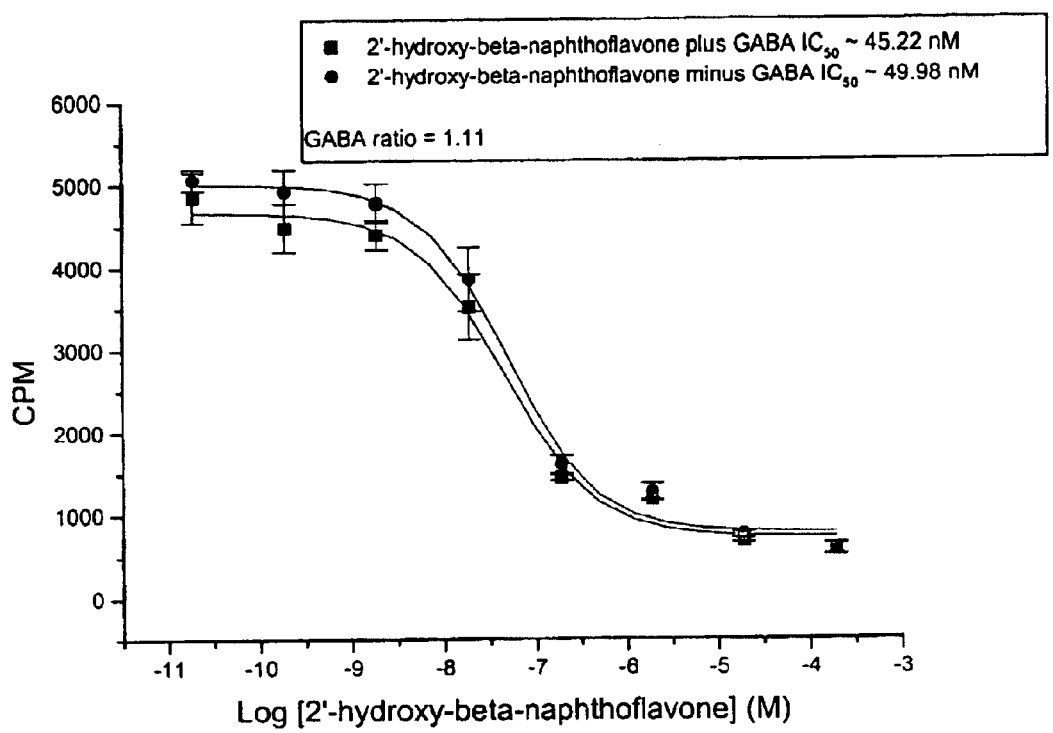

Of the twelve flavone derivatives studied (see FIG. 1B and Tables 2 and 3), the top five flavonoids with the strongest binding affinities contained a 2' OH group (determined by comparing $K_1$ values). This result demonstrated the importance of this side chain to the binding affinity of various flavone derivatives. Comparison of flavonoids differing in only the 2' carbon group demonstrated the effects of this group even more conclusively.

Comparison of Compounds 1 and 6

Compounds 1 and 6 were identical, except that Compound 1 contained a hydroxyl group at the 2' position, while Compound 6 contained a hydrogen at the 2' position.

Compound 1 demonstrated a $K_1$ value of 0.0011 μM and Compound 6 a $K_i$ value of 0.29 μM. Thus, the presence of a hydroxyl group in the 2' position resulted in a 260-fold difference in binding affinity between the two compounds.

Comparison of Compounds 2 and 7

Compounds 2 and 7 were identical, except that Compound 2 contained a hydroxyl group at the 2' position, while Compound 7 contained a hydrogen at the 2' position.

Compound 7 demonstrated a $K_1$ value of 1.28 μM and Compound 2 a $K_i$ value of 0.0076 μM. Thus, the presence of a hydroxyl group in the 2' position resulted in a 168-fold difference in binding affinity between the two compounds Comparison of Compounds 3, 11 and 12

Compounds 3 and 11 both contained a hydroxyl group at the 6 position, however, Compound 3 contained a hydroxyl group at the 2' position and Compound 11 contained a methoxyl group at the 2' position. Compound 12 did not contain a hydroxyl group at the 6 position, but did contain a methoxyl group at the 2' position.

Thus, substitution of a hydroxyl group for the 2' methoxyl group of Compound 12 ($K_1$ value of 12.01 μM) resulted in a $K_1$ value of 0.013 μM, an over 900-fold difference in the binding affinities of the two compounds, while the addition of a hydroxyl group on the 6 carbon (from Compound 12 to 11) resulted in only a minor difference between the $K_1$ values of the two compounds.

Comparison of Compounds 5 and 12

Compound 5 contained a hydroxyl group at the 2' position, while Compound 12 contained a methoxyl group at the 2' position.

This single modification between Compound 5 and Compound 12, the substitution of an hydroxyl group on the 2' carbon, resulted in a change in the $K_1$ value of from 12.01 μM to 0.15 μM, an 80-fold difference in the binding affinities of the two compounds.

Comparison of Compounds 5 and 9

Compound 5 contained a hydroxyl group at the 2' position, while Compound 9 contained a hydrogen at the 2' position.

The addition of a 2' hydroxyl group resulted in a change in the $K_i$ values from 6.858 μM to 0.19 μM, over a 30 fold-difference in the binding affinities between the two compounds.

Without exception, substitution of a hydroxyl group at the 2' carbon on flavonoid molecules led to significant increases in their respective binding affinities for the BZD-S. While not wishing to be bound by theory, these results strongly suggest that the 2' OH group on flavonoid molecules is one of the main residues responsible for the interaction between the ligand and the receptor subunits.

EXAMPLE 2

Determining the GABA Ratios of Selected Compounds

Owing to different intrinsic activities and pharmacological properties of various benzodiazepine ligands, the GABA shift experiment has been adopted widely to correlate the characterization of a test compound in vitro with its in vivo profile. Based on the observation that GABA enhances the binding affinity of benzodiazepine receptor agonists (Tallman et al., 1978), this protocol was developed by Braestrup and Nielsen. It was shown that agonists at the benzodiazepine receptor increased in their binding affinity in the presence of GABA, antagonists showed negligible enhancement, while inverse agonists were reciprocal to that of agonists. GABA ratios are thus useful in the prediction of potential benzodiazepine receptor agonists, inverse agonist and antagonists, with ratios <1, >1, and ~1 respectively.

In this study, 12 different flavonoids were assayed for their binding affinities with the benzodiazepine site on $GABA_A$ receptor, their $IC_{50}$ and $K_i$ values calculated and compared, taking into account their respective structures. Candidates for this experiment were chosen to draw special attention to the 2' hydroxyl group which differs only in one side branch, i.e., the presence or absence of the 2' hydroxyl group. After the correlation of structural differences with respective affinities, GABA ratios of the compounds were determined.

For the GABA shift experiment, competition assays were performed in a final concentration of 1 nM [$^3$H]-Ro15-1788, while the incubation mixture was identical to that prepared for the radio ligand receptor binding experiment described in Example 1. GABA ratios were determined by dividing the $IC_{50}$ of the test compound in the absence of GABA by the IC50 obtained in the presence of 10 μM GABA.

The GABA ratios of a number of BZD-S reference compound are listed in Table 4.

TABLE 4

GABA Ratios of Some Benzodiazepine Site Reference Compounds

| | $IC_{50}$ ratio without GABA/ | | with GABA) |
|---|---|---|---|
| Compound | $A_a$ | $B_b$ | $C_c$ |
| Agonist | | | |
| Diazepam | 2.9 | 2.3 | 2.0 |
| Flunitrazepam | 3.3 | 2.5 | 1.9 |
| Oxazepam | 2.7 | 2.4 | — |
| Antagonist | | | |
| Ro15-1788 | 1.1 | 1.2 | 0.9 |
| BCCP | 1.0 | 1.1 | — |
| Inverse agonist | | | |
| FG 7142 | 0.7 | 0.9 | 0.9 |
| DMCM | 0.7 | 0.5 | — |
| BCCM | 0.7 | 0.9 | 0.7 |
| BCCB | — | — | 0.5 |
| Ro15-4513 | — | — | 0.9 |

$_a$GABA shift determined in the presence of $10^{-4}$ M GABA with membranes from rat cerebral cortex (Mohler and Richards, 1981)
$_b$GABA shift determined in the presence of $10^{-5}$ M muscimol in rat cerebellar membranes (Braestrup et al., 1982)
$_c$GABA shift determined in the presence of $10^{-5}$ M GABA with membranes from rat cerebral cortex.

The results of the GABA shift experiment for 8 selected flavonoid compounds is listed in Table 5.

TABLE 5

GABA Ratio of Test Flavonoids

| Compound | Name | GABA ratio |
|---|---|---|
| 1 | 5,7,2'-trihydroxy-6,8-dimethoxyflavone (K36) | 1.20 |
| 2 | 5,7,2'-trihydroxy-6-methoxyflavone (K38) | 1.27 |
| 3 | 6,2'-dihydroxyflavone | 0.89 |
| 4 | 2'-hydroxy-beta-naphthoflavone | 1.06 |
| 5 | 2'-hydroxyflavone | 1.17 |
| 6 | 5,7-dihydroxy-6,8-dimethoxyflavone (SB-D83) | N/A |
| 7 | 5,7-dihydroxy-6-methoxyflavone (K7) | 1.09 |
| 8 | 5,7-dihydroxy-8-methoxyflavone (Wogonin) | 1.03 |

It should be noted that the use of a different radioligand in this assay results in varying $IC_{50}$ values, hence $IC_{50}$ values obtained here are for calculation of the GABA ratio of the respective test compounds only.

As shown in Table 5, the GABA ratio of the compounds were in the range of 1.10–1.30, with the exception of Compound 3, 6,2'-dihydroxyflavone. Such values suggest that this class of compounds may exhibit partial agonistic characteristics. As for Compound 3, with a GABA ratio of 1.02, a pharmacological profile between an antagonist and a partial agonist might be expected. It should be noted, however, that the GABA ratio only provides an estimate of a compound's intrinsic activity. Absent in vivo or electrophysiology data for a class of compounds, a comparison of GABA values between classical benzodiazepine ligands and non-benzodiazepine compounds demonstrating BZD-R affinity requires further validation to confirm the actual characteristics.

EXAMPLE 3
Measuring the BZD-S Binding Affinity of 5,7,2'-trihydroxy-6-8-dimethoxyflavone (K36)

5,7,2'-trihydroxy-6-8-dimethoxyflavone (K36) was dissolved in dimethylsulfoxide (DMSO, Acros Organics, Belgium) and assayed at less than 0.2% final DMSO concentration. DMSO at a concentration less than 0.5% showed no significant effects on the BDZ-R assay. The radioreceptor binding assay was performed as described previously (Schacht and Baecker, 1982 and in Vogel, et al., 1997).

Whole forebrains from decapitated Sprague-Dawley rats (approximately 200 g) were homogenized to give the crude synaptosomal fraction. In the assay procedure, 45 μl of the crude synaptosomal fraction (0.8 mg/ml) were added to 238 μl 0.05 M Tris-HCl (pH 7.4) with or without non-labeled test drugs. Samples were incubated in duplicate for 30 minutes at 4° C. In the competitive assay, 1 nM[$^3$H]flunitrazepam was employed and non-specific binding was determined by the addition of 300 μM diazepam. After incubation, the reaction was rapidly stopped by filtration through Millipore GF/B filter and washed twice with 5.0 ml ice-cold 0.05 M Tris-HCl buffer before drying.

In the saturation assay, twelve concentrations (1.33–125.00 nM) of [$^3$H]flunitrazepam were analyzed to determined the $K_d$ value of [$^3$H]flunitrazepam. The dissociation constant ($K_1$) of the test drugs was determined from the following formula: $K_1 IC_{50}/[1+[^3H]/K_d]$. The data are shown below in Table 6.

TABLE 6

| Inhibition of $^3$H-Flunitrazepam (μM) | |
|---|---|
| Compound | Ki |
| diazepam | 9.5 nM |
| K36 | 1.1 nM |

EXAMPLE 4
In Vivo Studies To Determine the Anxiolytic, Sedative and Myorelaxant Effects of 5,7, 2'-trihydroxy-6-8-dimethoxyflavone (K36)

Male ICR mice (18–20 g) were obtained from the Animal Care Centre, HKUST, and were randomly distributed into different experimental groups. Mice were housed in groups of four to five with food and water ad libidum and maintained in a 12:12 hr light/dark cycle. Experiments were conducted between 0830 and 1200 hours.

Hole-Board Test

The hole-board apparatus was a wooden box (60×60×30 cm) consisting of four holes (3 cm in diameter) equally spaced in the floor. The entire apparatus was painted white. Mice were placed individually at the center of the floor and the number of head-dips, the time spent head-dipping and the number of rearings were counted in a 5-minute period (File and Pellow, 1985). After each trial, the floor of the apparatus was wiped and dried thoroughly with paper towel to remove traces of previous paths. An increase in the number and time spent head-dipping, and the number of rearings reflect a greater exploratory activity. A decrease of these three parameters as compared to control reveals a sedative behavior (Nolan and Parkes, 1973; File and Wardill, 1975,File and Pello, 1986).

Hole-Board Test

Figure 5:
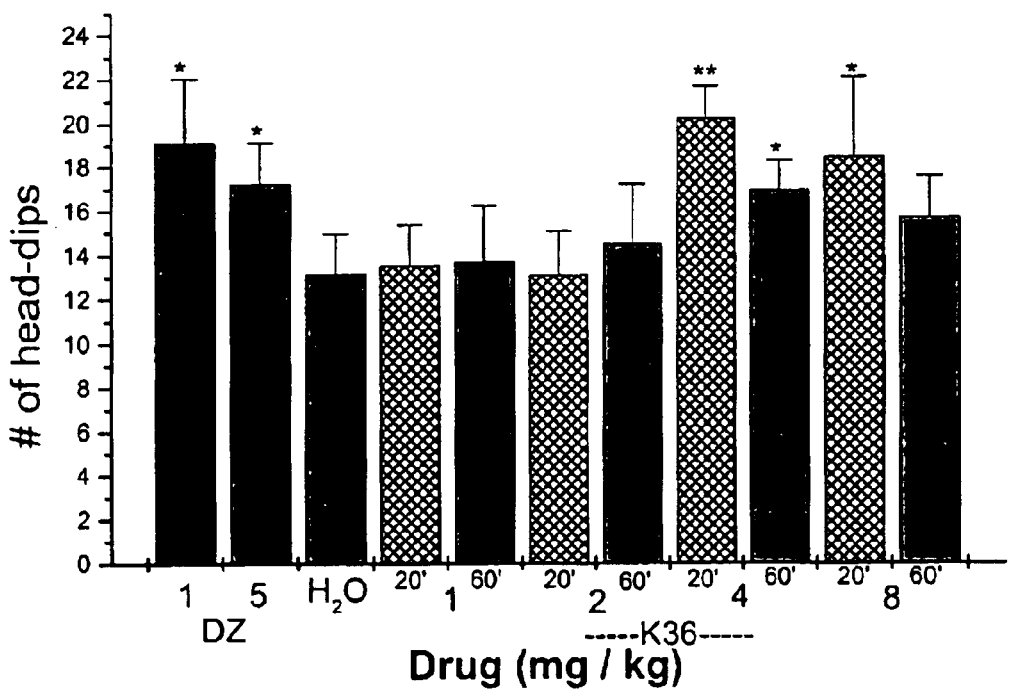
FIG. 5 is a bar graph illustrating the mean percentage of head dips of mice at twenty (20) minutes and sixty (60) minutes after treatment with doses of 5,7,2'-trihydroxy-6,8-dimethoxyflavone (K36) ranging from 1.0 mg/kg–8.0 mg/kg. Mice treated with diazepam (DZ) and water were utilized as controls.
Figure 6:
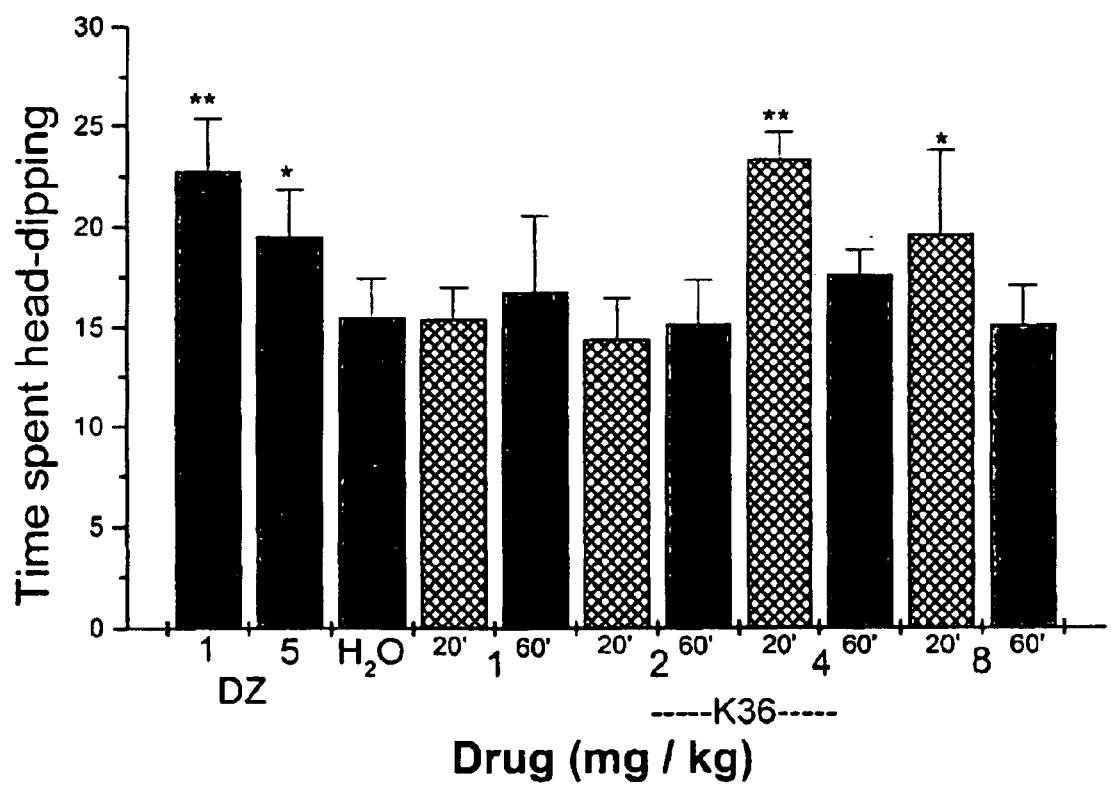
FIG. 6 is a bar graph illustrating the mean percentage of head dips of mice at twenty (20) minutes and sixty (60) minutes after treatment with doses of 5,7,2'-trihydroxy-6,8-dimethoxyflavone (K36) ranging from 1.0 mg/kg–8.0 mg/kg. Mice treated with diazepam (DZ) and water were utilized as controls.
Figure 7:
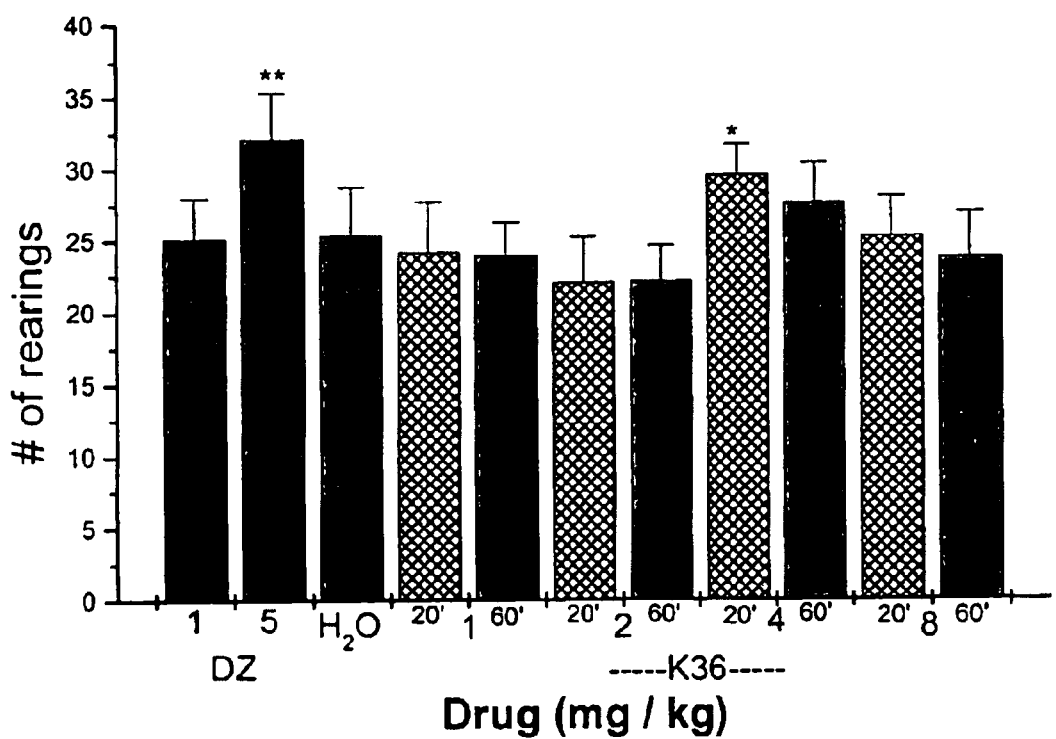
FIG. 7 is a bar graph illustrating the mean percentage of rearings of mice at twenty (20) minutes and sixty (60) minutes after treatment with doses of 5,7,2'-trihydroxy-6,8-dimethoxyflavone (K36) ranging from 1.0 mg/kg–8.0 mg/kg. Mice treated with diazepam (DZ) and water were utilized as controls.

As seen in Table 7, acute administration of 4 mg/kg K36 twenty minutes after dosage resulted in a significant increase in the number of head-dips, time spent head-dipping and the number of rearings. While 8 mg/kg of K36 increased the number of head-dips and the time spent head-dipping, acute administration of diazepam at both dosage increased number of head-dips, time spent head-dipping and the number of rearings (Table 7, FIGS. 5, 6 & 7).

TABLE 7

Exploratory Behavior of Mice Treated With Various Dosages of 5,7,2'-Trihydroxy-6,8-dimethoxyflavone (K36)

| DRUG | Time (min) | Number of head dips | Time spent head-dipping | Number of rearings |
|---|---|---|---|---|
| DZ | | | | |
| 1 mg/kg | | 19.12 ± 2.92* | 22.75 ± 2.59 | 25.13 ± 2.85 |
| 5 mg/kg | | 17.25 ± 1.89* | 19.50 ± 2.33* | 32.16 ± 3.15 |
| Vehicle | | 13.19 ± 1.76 | 15.50 ± 1.96 | 25.38 ± 3.39 |
| K36 | | | | |
| 1 mg/kg | 20 | 13.56 ± 1.81 | 15.38 ± 1.59 | 24.19 ± 3.53 |
| 1 mg/kg | 60 | 15.75 ± 2.53 | 16.75 ± 3.78 | 23.94 ± 2.34 |
| 2 mg/kg | 20 | 13.13 ± 1.96 | 14.56 ± 2.04 | 22.06 ± 3.17 |
| 2 mg/kg | 60 | 14.50 ± 2.73 | 15.13 ± 2.20 | 22.13 ± 2.46 |
| 4 mg/kg | 20 | 20.25 ± 1.42** | 23.35 ± 1.28** | 29.54 ± 2.09* |
| 4 mg/kg | 60 | 16.95 ± 1.33 | 17.56 ± 1.20 | 27.56 ± 2.79 |
| 8 mg/kg | 20 | 18.46 ± 3.65* | 19.55 ± 4.23* | 25.26 ± 2.74 |
| 8 mg/kg | 60 | 15.72 ± 1.86 | 15.06 ± 1.98 | 23.75 ± 3.18 | n = 16 per group
*p < 0.1, p < 0.05, *p < 0.01, ****p < 0.001, significantly different from control, Dunnett's t test after one way ANOVA.

Mean (±S.E.M.) total number of head-dips, time spent head-dipping, and number of rearings in mice during a 5-min test, 20 minutes, K36 only, and 1 hour after oral administration acutely with vehicle ($H_2O$, pH 7), diazepam (DZ), or 5,7,2'-trihydroxy-6,8-dimethoxyflavone (K36). n=16 per group *p <0.1, significantly different from control, Dunnett's t test after one way ANOVA Elevated Plus-Maze Test The maze had two opposite arms, 25×10 cm, crossed with two enclosed arms of the same dimension but having 20 cm high walls. The arms were connected with a central platform, 5×5 cm, giving the apparatus the shape of a plus sign. The maze was kept in a dimly-lit room and elevated 40 cm above ground. Following the hole-board test, mice were placed individually at the center of the maze facing an enclosed arm. The number of entries and the time spent in the open arms and closed arms were recorded in a 5-minute period. An arm entry was defined as having all four paws inside the arm. This method allowed the separation of directed exploratory (head-dipping) from locomotor activity and rearing (File and Wardill, 1975) and increased the overall activity in the plus-maze (Pellow et al., 1985; Lister 1987). The total number of arm entries provided a measure of general activity and a selective increase in the parameters corresponding to open arms reveals an anxiolytic effect (Pellow et al., 1985, Lister, 1987).

Elevated Plus-Maze

Figure 3:
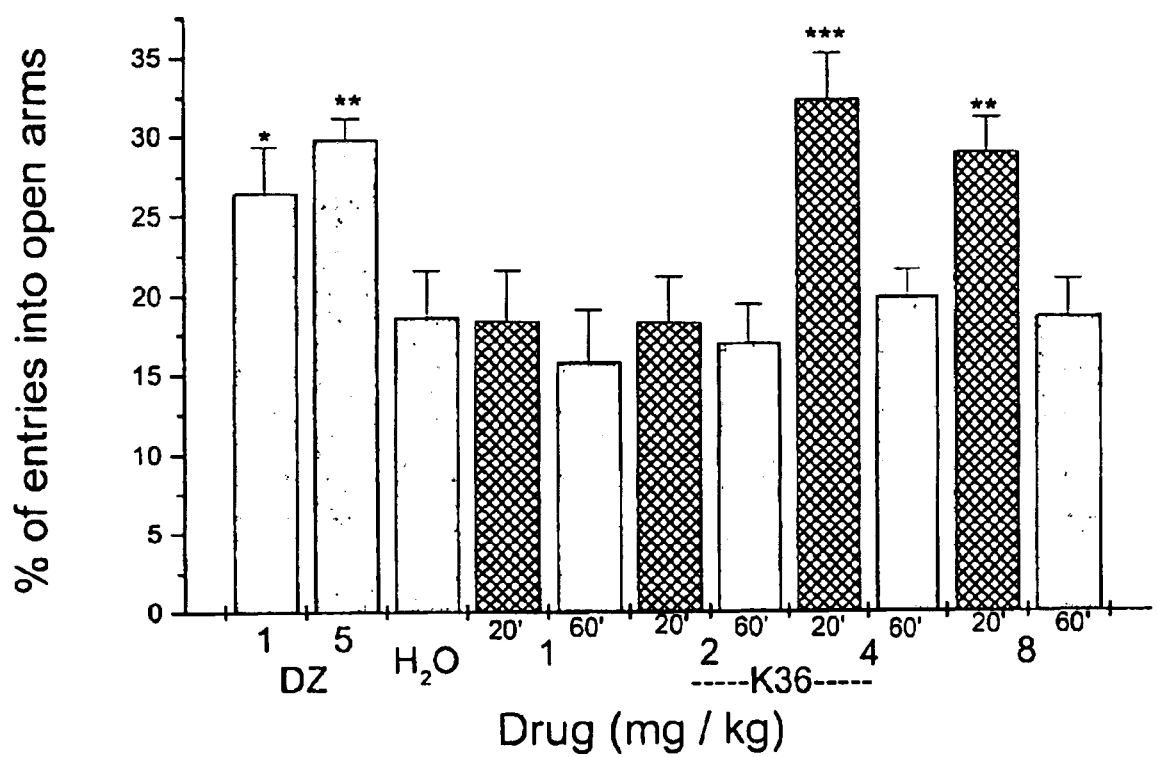
FIG. 3 is a bar graph illustrating the mean percentage of arm entries of mice at twenty (20) minutes and sixty (60) minutes after treatment with doses of 5,7,2'-trihydroxy-6,8-dimethoxyflavone (K36) ranging from 1.0 mg/kg–8.0 mg/kg in an elevated plus-maze. Mice treated with diazepam (DZ) and water were utilized as controls.
Figure 4:
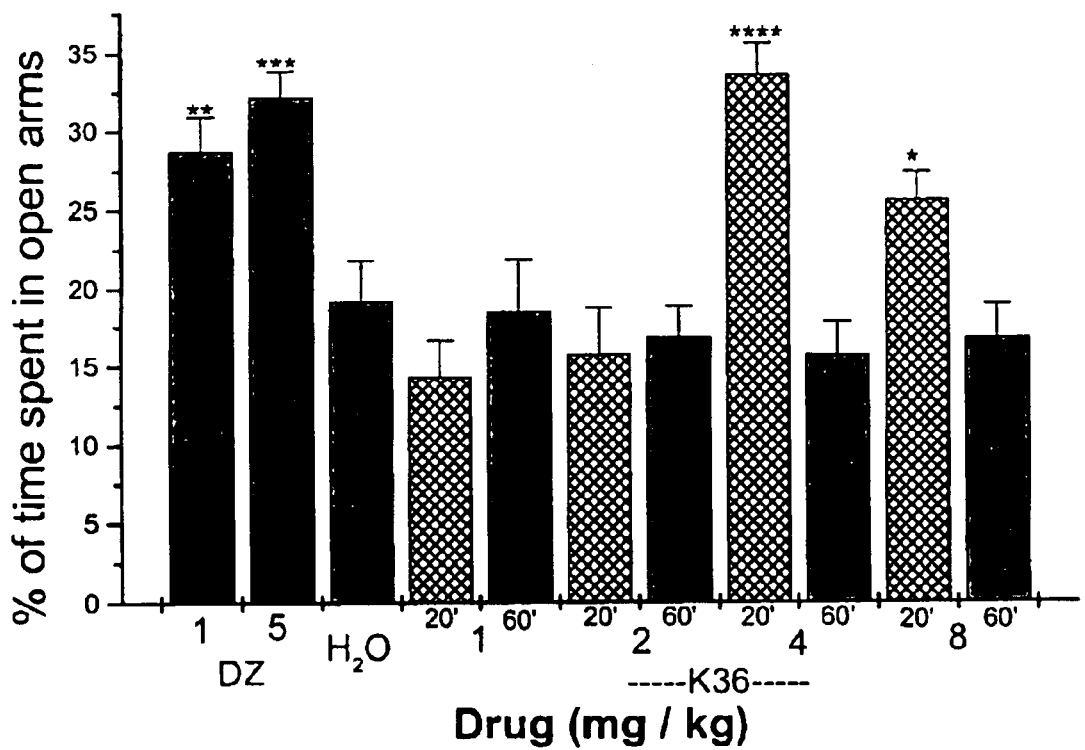
FIG. 4 is a bar graph illustrating the mean total percentage of time spent by mice at twenty (20) minutes and sixty (60) minutes after treatment with doses of 5,7,2'-trihydroxy-6,8-dimethoxyflavone (K36) ranging from 1.0 mg/kg–8.0 mg/kg in the open arms of an elevated plus-maze. Mice treated with diazepam (DZ) and water were utilized as controls.

K36, at 4.0 and 8.0 mg/kg, resulted in a significant increase in both time spent in open arms and entries made into open arms twenty minutes after dosage. Other dosage regimens did not alter these parameters when compared to the control. DZ (1.0 and 5.0 mg/kg) treated mice exhibited a dose dependent increase in the time spent in open arms and the entries made into open arms in comparison to control mice. At 4.0 mg/kg, K36 caused more anxiolysis when compared to either dosage of diazepam (Table 5, FIGS. 3 & 4).

TABLE 8

Behavior of Mice Treated With Various Dosages of 5,7,2'-Trihydroxy-6,8-dimethoxyflavone (K36) in Elevated Plus-Maze

| DRUG | Time (min) | % of entries into open arms | % of time spent in open arms |
|---|---|---|---|
| DZ | | | |
| 1 mg/kg | | 26.48 ± 2.83* | 28.71 ± 2.27*** |
| 5 mg/kg | | 29.85 ± 1.29** | 32.24 ± 1.56**** |
| Vehicle | | 18.70 ± 2.83 | 16.28 ± 1.96 |
| K36 | | | |
| 1 mg/kg | 20 | 18.39 ± 3.14 | 14.28 ± 2.36 |
| 1 mg/kg | 60 | 18.51 ± 3.34 | 15.80 ± 3.29 |
| 2 mg/kg | 20 | 18.30 ± 2.78 | 15.74 ± 3.00 |
| 2 mg/kg | 60 | 16.91 ± 2.49 | 16.84 ± 1.99 |
| 4 mg/kg | 20 | 32.28 ± 2.91*** | 33.55 ± 2.09**** |
| 4 mg/kg | 60 | 19.90 ± 1.63 | 15.69 ± 2.09 |
| 8 mg/kg | 20 | 28.90 ± 2.23** | 25.62 ± 1.73* |
| 8 mg/kg | 60 | 18.67 ± 2.24 | 16.76 ± 2.19 | n = 16 per group
*p < 0.1, p < 0.05, *p < 0.01, ****p < 0.001, significantly different from control, Dunnett's t test after one way ANOVA.

Mean (±S.E.M.) total percentage of arm entries and time spent in open arms of an elevated plus-maze in mice during a 5-min test, 20 minutes and 1 hour after oral administration acutely with vehicle ($H_2O$, pH 7), diazepam (DZ), or 5,7, 2'-trihydroxy-6-8-dimethoxyflavone (K36).

Horizontal Wire Test

Mice were lifted by the tail and allowed to grasp a horizontally strung wire (1 mm diameter, 15 cm long and placed 25 cm above floor) with their forepaws and released (Bonetti et al., 1982). Each mouse was tested prior to drug administration and only mice successful in grasping the wire with their hind limbs are tested and scored for their ability to grasp the wire. A myorelaxant drug impairs the ability of the mice to grasp the wire, and such muscle relaxation is commonly associated with sedation.

Horizontal Wire Test

Figure 8:
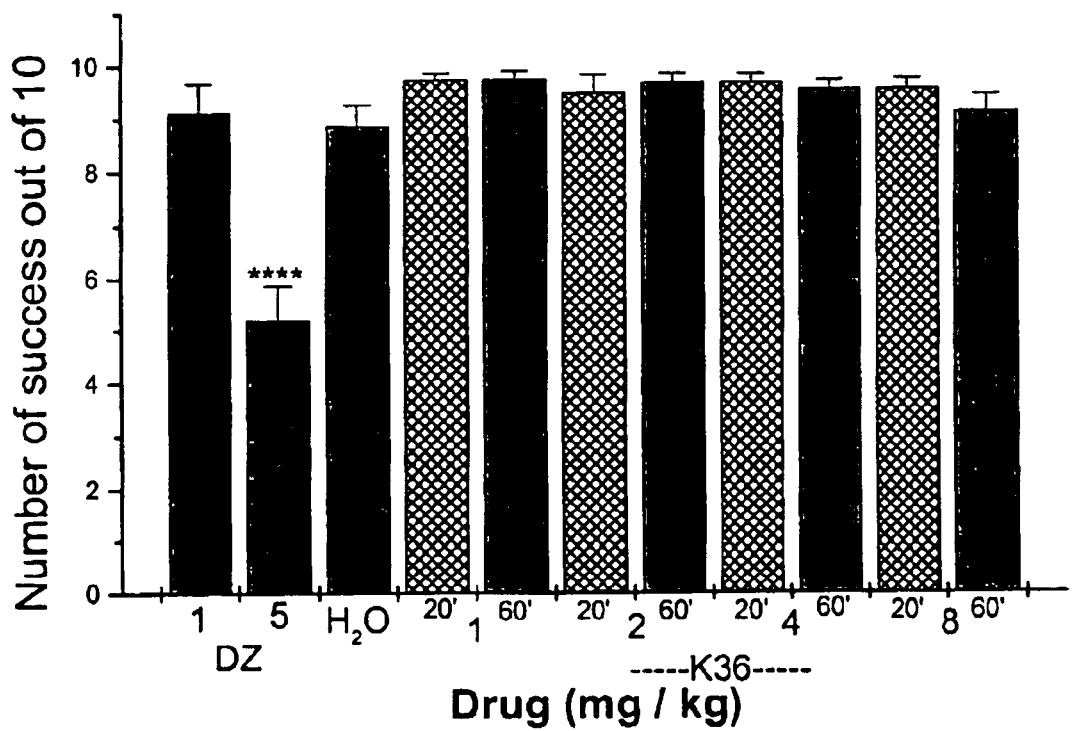
FIG. 8 is a bar graph illustrating the mean total number of successful graspings of wire, out of 10 attempts, in the horizontal wire test of mice at twenty (20) minutes and sixty (60) minutes after treatment with doses of 5,7,2'-trihydroxy-6,8-dimethoxyflavone (K36) ranging from 1.0 mg/kg–8.0 mg/kg. Mice treated with diazepam (DZ) and water were utilized as controls.
Figure 9:
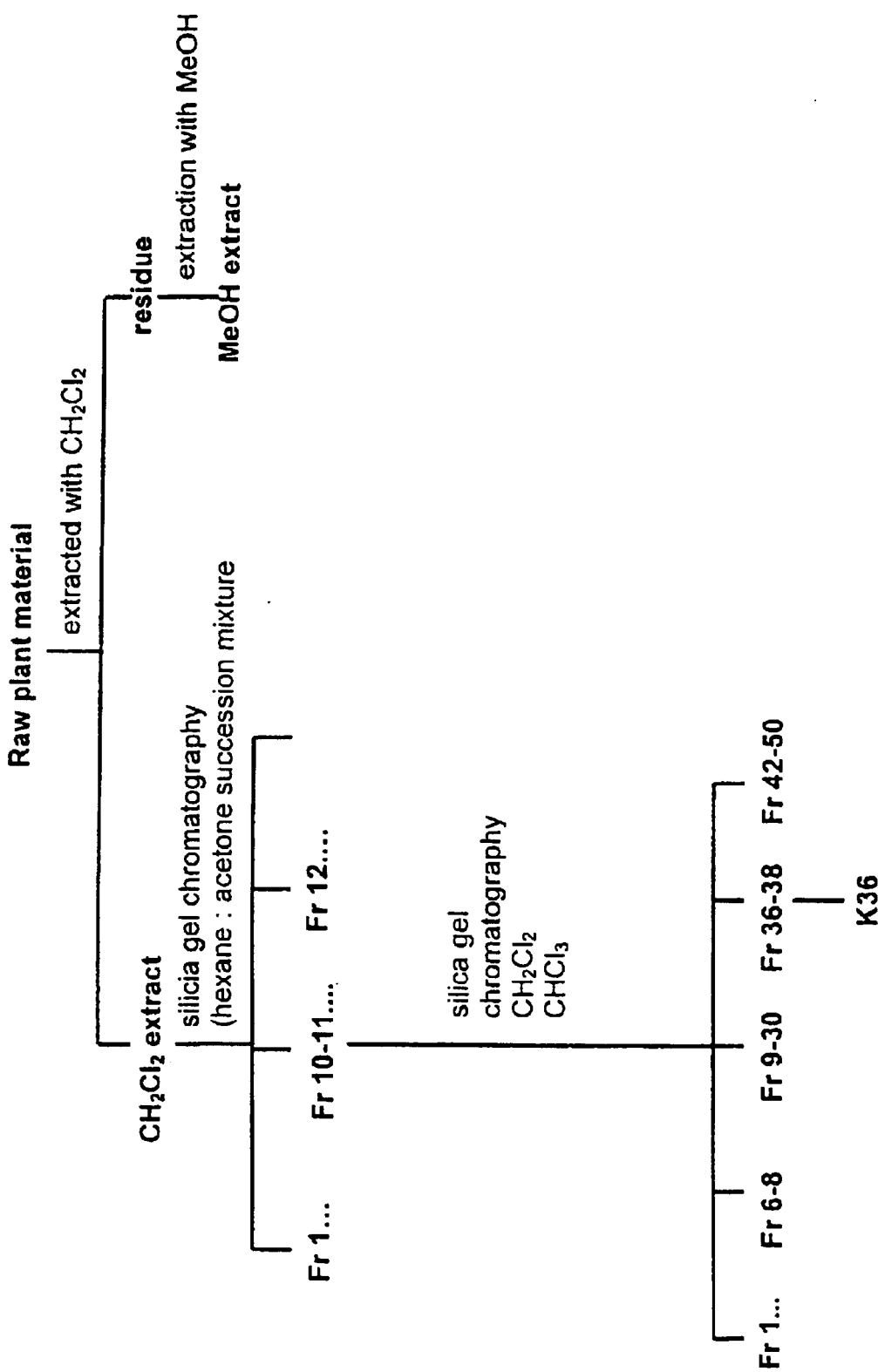
FIG. 9 is a schematic illustration of a method of preparing 5,7,2'-trihydroxy-6,8-dimethoxyflavone (K36) from the roots of *Scutellaria baicalensis* Georgi.

Only the mice treated with 5.0 mg/kg diazepam exhibited significant impairment the ability to grasp the wire when compared to control. The ability of the mice remained unchanged (FIG. 8).

Statistical Analysis

The data are expressed as mean SEM for each treatment group. The data obtained from each response measures were subjected to one way analysis of variance (ANOVA) and multiple group comparisons were made by Dunnett's t test for only those responses which yielded significant treatment effects in the ANOVA test.

From the above results, K36 has been shown to possess in vivo effects, indicating the ability of K36 itself or its bioactive metabolites to penetrate the blood brain barrier after absorption. However, its anxiolytic effect was apparent only 20 minutes after drug administration at the selected dosage regimens. Possible explanations remain to be identified. Nevertheless, anxiolysis of K36 was found to be more marked than that of the common benzodiazepine anxiolytic agent diazepam at the tested dosage.

In the hole-board test where cognitive/sedative effects were assayed, diazepam and the higher doses of K36 caused significant increase in the number of head-dips, time spent head-dipping and the number of rearings. Accordingly, neither diazepam nor K36 caused significant decrease in these parameters, suggesting the lack of sedative effects at the dosage regimen.

In the horizontal wire test, only mice treated with the higher dose of diazepam exhibited a reduced ability to grasp the wire, while the ability of the other mice remained unchanged. This represents the compromised side-effect of diazepam at this dosage for its anxiolytic effects.

Overall, K36 has been shown to possess anxiolytic effects without the sedative and myorelaxation effects often seen in classical benzodiazepines and other non-benzodiazepine anxiolytic agents at the dosage regimen.

EXAMPLE 5

Preparation of 5,7,2'-Trihydroxy-6-8-dimethoxyflavone (K36)

The roots of Scutellaria baicalensis Georgi (2.0 kg) were ground into powder and extracted three times, each time with 5.0 L of dichloromethane (DCM), at room temperature. The extract was filtered with Whatman No. 1 filter paper, and then the residue was extracted three times, each time with 5.0 L of methanol ($CH_3OH$). The filtered extracts were concentrated in a rotary vacuum evaporator at 60° C. The concentrated DCM extract was subjected to silica gel (Merck, 70–230 mesh, 800 g) chromatography by elution successively with 1.5 L of 20:1, 10:1, 8:1, 5:1, 3:1 and 1:1 hexane-acetone mixtures. Guided by the TLC (Merck, Silica gel 60) profiles, the collected fractions were pooled into fifteen (15) fractions of about 100 ml each. When assayed with the benzodiazepine receptor (BDZ-R), Fractions 10–12 showed binding activity. Fraction 10 and Fraction 11 were pooled together and further subjected to silica gel (100 g) chromatography by elution with 1.0 L DCM and chloroform. The effluent (20 ml each fraction) was pooled into fifty fractions. Fractions 36 to 38 were pooled together and recrystallized in methanol to yield 5,7,2'-trihydroxy-6,8-dimethoxyflavone (5,7,2'-trihydroxy-6-8-dimethoxyflavone) (10 mg). After purification, the chemical structure of 5,7,2'-trihydroxy-6-8-dimethoxyflavone was determined by the EI-mass and $^1$H-NMR (400 MHZ), and is depicted below:

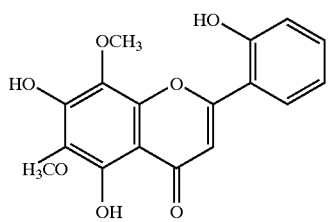

and its physical and chemical specifications are as follows:
Chemical formula:
5,7,2'-trihydroxy-6,8-dimethoxyflavone
Physical appearance:
Yellow needles from methanol, mp 262–263° C., Mg+HCl:Orange yellow.
Spectra:
MS m/e 330 ($M^+$). Anal. Calcd. $C_{17}H_{14}O_7$: C, 61.82; H, 4.27. Found: C, 61.70; H, 4.38. UV $\lambda_{max}$ nm (log $\epsilon$): (MeOH) 275(4.14), 336(4.18). IR (KBr) $v_{max}$ $cm^{-1}$: 3456 (OH), 1658(conjugated CO), 1610, 1578(arom. C=C).
$^1$H-NMR (DMSO-$d_6$): 3.77(3H,s,6-$OCH_3$), 3.84(3H, s, 8-$OCH_3$), 7.04(1H, br t, J=8.0 Hz, 4'-H), 7.06(1H, s, 3-H), 7.07(1H, br d, J=8.0 Hz, 3'-H), 7.42(1H, dt, J=1.5, 8.0 Hz, 5'-H), 7.86(1H,dd, J=1.5, 8.0 Hz, 6'-H), 12.74(1H,s, 5-OH).
$^{13}$C-NMR (DMSO-$d_6$): 161.2(C-2), 108.6(C-3), 182.4(C-4), 148.2(C-5), 131.4(C-6), 151.0(C-7), 127.9(C-8), 145.6 (C-9), 103.0(C-10), 117.4(C-1'), 156.8(C-2'), 117.1(C-3'), 132.9(C-4'), 119.6(C-5'), 128.2(C-6'), 61.2(C-6-$OCH_3$), 60.2(C-8-$OCH_3$).

EXAMPLE 6

Preparation of 5,7,2'-Trihydroxy-6-8-dimethoxyflavone-Supercritical Fluid Extraction (SFE) Method The pulverized sample (100 g) was packed into a 1000 ml sample cartridge. Methanol or 70% methanol (100 ml, 200 ml and 300 ml, respectively was added), and 2000 ml liquid carbon dioxide was used as extraction solvent. The extraction temperature was set at 40, 50, 60 and 70° C., respectively. Liquid carbon dioxide at high pressure (200, 300 and 400 bar) was then allowed to flow into the sample cartridge. When the pressure reached 200, 300, and 400 bar, the vent valve of the extractor was opened immediately and carefully, so that the soluble fraction was collected through tubing to a test tube filled with 1000 ml methanol. The extraction process was run for 10~15 minutes, and was repeated three times. The crude extract was obtained by reduced pressure evaporation and then subjected to column chromatography over silica gel and eluted with chloroform-methanol.

The concentrated extract was subjected to silica gel (Merck, N.J. 70–230 mesh, 800 g) chromatography by elution successively with 1.5 L of 20:1, 10:1, 8:1, 5:1, 3:1 and 1:1 hexane-acetone mixtures. Guided by the TLC (Merck, N.J., Silica gel 60) profiles, the collected fractions were pooled into fifteen (15) fractions of about 100 ml each. When assayed with the benzodiazepine receptor (BDZ-R), Fractions 10–12 showed binding activity. Fraction 10 and Fraction 11 were pooled together and further subjected to silica gel (100 g) chromatography by elution with 1.0 L DCM and chloroform. The effluent (20 ml each fraction) was pooled into fifty fractions. Fractions 36 to 38 were pooled together and recrystallized in methanol to yield 5,7,2'-trihydroxy-6,8-dimethoxyflavone (K36) (10 mg).

EXAMPLE 7

Different Substitutions at the 2' Carbon Alters Binding Affinity of Flavonoid Derivatives

TABLE 9

| IC50 Values of 2' Flavonoid Derivatives Compound Inhibition of [3H]-flunitrazepam ($\mu$M) | |
|---|---|
| | IC50 |
| 2'chloroflavone | <100 $\mu$M |
| 8-bromo,2',6-dichloroflavone | <100 $\mu$M |
| 2',6-dichloro,7-methoxyflavone | <100 $\mu$M |
| 2',6-methoxyflavone | <100 $\mu$M |
| 6-bromo,2'-chloroflavone | <100 $\mu$M |
| 2',6-dichloroflavone | <100 $\mu$M |
| 2'-nitroflavone | <100 $\mu$M |
| 2'-amino, 6-methoxyflavone | 2 $\mu$M |
| 2'-chloro, 6-methoxyflavone | <100 $\mu$M |
| 2'-chloro, 6-hydroxyflavone | <100 $\mu$M |

From previous experiments, it has been demonstrated that flavonoids with a hydroxyl group at the 2' carbon exhibit enhanced binding affinities against the benzodiazepine binding site. Therefore, flavonoids with different substituents, i.e. -Cl, —$NO_2$, and —$NH_2$, at the 2' carbon were organically synthesized for further investigation. When these flavonoids were assayed, it was found that, only the flavonoid with an —$NH_2$ substitution had significant affinity for the benzodiazepine binding site (data not shown). As the non-bonding electrons of the —OH and —NH$_2$ substitutions donate electron density to their respective benzene ring through σ bonding, the hydrogen(s) is rendered a partial positive charge. While not wishing to be bound by theory, this resonance donation is a possible explanation for the observed enhanced binding affinities of the flavonoids with the two substitutions. However, with the halogen substituents, which are strongly electronegative, would withdraw electron density from the carbon atom through sigma bonding (inductive withdrawal). This difference may account for the variation of binding affinities of this two distinct group of substituents.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of preventing or treating a BZD-S associated syndrome in a patient in need thereof, comprising administering to the patient an effective non-toxic dose of a compound comprising:

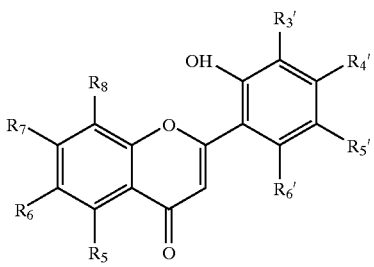

Formula I or a physiological salt thereof, wherein:
R$_7$ is H or OH and
R$_5$, R$_6$, R$_8$, R$_3$', R$_4$', R$_5$' and R$_6$' are each, independently, H, OH, a C$_1$–C$_6$ alkyl, a C$_1$–C$_6$ alkenyl or a C$_1$–C$_6$ alkoxy; and wherein the syndrome is anxiety or convulsions.

2. The method of claim 1, wherein R$_5$ is OH.
3. The method of claim 1, wherein R$_6$ is OH.
4. The method of claim 1, wherein R$_7$ is OH.
5. The method of claim 1, wherein R$_5$ and R$_6$ are both OH.
6. The method of claim 1, wherein R$_6$ and R$_7$ are both OH.
7. The method of claim 1, wherein R$_5$ and R$_7$ are both OH.
8. The method of claim 1, wherein the dose is administered in a single aliquot.
9. The method of claim 1, wherein the dose is administered in two or more aliquots.
10. A method of preventing or treating a BZD-S associated syndrome in a patient in need thereof, comprising administering to the patient an effective non-toxic dose of a compound comprising 5,7,2'-trihydroxy-6,8-dimethoxyflavone or a physiologically acceptable salt thereof; wherein the syndrome is anxiety or convulsions.
11. The method of claim 1, wherein R$_5$, R$_6$ and R$_7$ are all OH.
12. The method of claim 1, wherein R$_6$ is methoxy.
13. The method of claim 1, wherein R$_8$ is methoxy.
14. The method of claim 1, wherein R$_6$ and R$_8$ are both methoxy.
15. A method of preventing or treating a BZD-S associated syndrome in a patient in need thereof, comprising administering to the patient an effective non-toxic dose of a compound comprising:

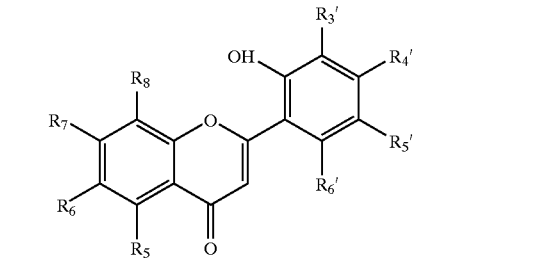

Formula I or a physiological salt thereof, wherein:
R$_7$ is H or OH and
R$_{1\ 5}$, R$_6$, R$_8$, R$_3$' and R$_4$' are each, independently, H, OH, a C$_1$–C$_6$ alkyl, a C$_1$–C$_6$ alkenyl or a C$_1$–C$_6$ alkoxy; and wherein the syndrome is anxiety or convulsions.

16. A pharmaceutical package comprising one or more containers filled with a compound comprising:

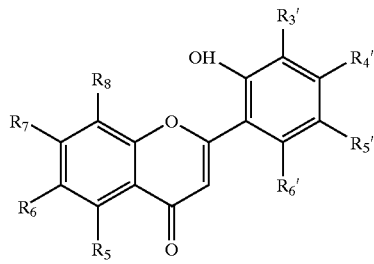

Formula I or a physiological salt thereof, wherein:
R$_7$ is H or OH and
R$_5$, R$_6$, R$_8$, R$_3$', R$_4$', R$_5$' and R$_6$' are each, independently, H, OH, a C$_1$–C$_6$ alkyl, a C$_1$–C$_6$ alkenyl or a C$_1$–C$_6$ alkoxy.

17. The package of claim 16 further comprising instructions for using the compound in the prevention or treatment of anxiety.
18. The package of claim 16 further comprising instructions for using the compound in the prevention or treatment of convulsions.

* * * * *

UNITED STATES PATENT AND TRADEMARK OFFICE
CERTIFICATE OF CORRECTION

PATENT NO. : 6,740,677 B2
DATED : May 25, 2004
INVENTOR(S) : Hong Xue et al.

Page 1 of 1

It is certified that error appears in the above-identified patent and that said Letters Patent is hereby corrected as shown below:

Column 20,
Lines 12-22, delete the structural formual following "a compound comprising" and appearing below,

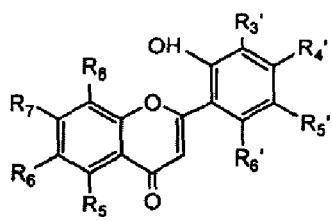 and substitute therefor: 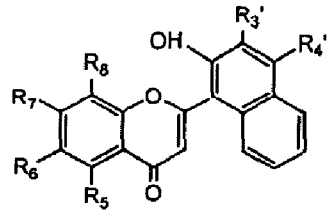

Line 26, delete the first term "$R_{1\,5}$" and substitute therefor -- $R_5$ --.

Signed and Sealed this

Thirtieth Day of November, 2004

JON W. DUDAS
*Director of the United States Patent and Trademark Office*